United States Patent
Fritz et al.

(10) Patent No.: US 6,835,177 B2
(45) Date of Patent: Dec. 28, 2004

(54) ULTRASONIC BLOOD VESSEL MEASUREMENT APPARATUS AND METHOD

(75) Inventors: Terry Fritz, Boise, ID (US); Helmuth Fritz, Yucaipa, CA (US)

(73) Assignee: Sonosite, Inc., Bothell, WA (US)

( * ) Notice: Subject to any disclaimer, the term of this patent is extended or adjusted under 35 U.S.C. 154(b) by 0 days.

(21) Appl. No.: 10/682,699

(22) Filed: Oct. 9, 2003

(65) Prior Publication Data

US 2004/0116808 A1 Jun. 17, 2004

Related U.S. Application Data

(63) Continuation-in-part of application No. 10/407,682, filed on Apr. 7, 2003.
(60) Provisional application No. 60/424,471, filed on Nov. 8, 2002, provisional application No. 60/424,465, filed on Nov. 8, 2002, provisional application No. 60/424,464, filed on Nov. 8, 2002, provisional application No. 60/424,463, filed on Nov. 8, 2002, and provisional application No. 60/424,027, filed on Nov. 6, 2002.

(51) Int. Cl.[7] .............................. A61B 8/00; G06K 4/00
(52) U.S. Cl. ........................ 600/443; 382/128; 382/273
(58) Field of Search ................................ 600/437, 438, 600/443, 447, 463, 466–467; 128/916; 382/128, 130, 131, 173, 256, 257, 262, 266, 273–274

(56) References Cited

U.S. PATENT DOCUMENTS

| | | | |
|---|---|---|---|
| 4,945,478 A | 7/1990 | Merickel et al. ........ | 364/413.22 |
| 5,203,337 A | 4/1993 | Feldman ................. | 128/662.06 |
| 5,345,938 A | 9/1994 | Nishiki et al. ......... | 128/660.04 |
| 5,411,028 A | 5/1995 | Bonnefous ............. | 128/661.08 |
| 5,520,185 A | 5/1996 | Soni et al. ............. | 128/661.08 |
| 5,533,510 A | 7/1996 | Koch, III et al. ....... | 128/660.07 |
| 5,544,656 A | 8/1996 | Pitsillides et al. ..... | 128/661.04 |
| 5,569,853 A | 10/1996 | Mignot ........................ | 73/603 |
| 5,669,382 A | 9/1997 | Curwen et al. ............ | 12/653.1 |
| 5,687,737 A | 11/1997 | Branham .................... | 128/710 |
| 5,712,966 A | 1/1998 | Nadachi ..................... | 395/128 |
| 5,724,973 A | 3/1998 | Spratt .................... | 128/661.03 |
| 5,800,356 A | 9/1998 | Criton et al. ............... | 600/441 |
| 5,952,577 A | 9/1999 | Passi .......................... | 73/618 |

(List continued on next page.)

*Primary Examiner*—Francis J. Jaworski
(74) *Attorney, Agent, or Firm*—Fulbright & Jaworski LLP

(57) ABSTRACT

An apparatus and method for determining the apparent intima-media thickness (IMT) of arteries through acquisition and analysis of ultrasound images comprising an array of pixel intensities. An acquired image may be referenced, determining threshold values relating to the intensity of pixels forming images of portions of an artery wall, particularly the lumen, media, and adventitia. A datum, or datums, may be established across multiple columns of pixels bounding the portion of the image containing either the lumen/intima boundary, the media/adventitia boundary, or both. The datums may be approximate the shape of one more of the lumen, intima, media, and adventitia. Within a bounded portion of the image, a method may search for intensity gradients having characteristics indicating the gradients represent probable locations of the lumen/intima and media/adventitia boundaries. A valid gradient may be identified by its proximity to a characteristic point on a graph of pixel intensities or to a datum line, by an intensity above or below a threshold, or both. An IMT measurement is calculated based on the location of the lumen/intima and media/adventitia boundaries. An IMT measurement may be adjusted for sloping or tapering of an artery wall. Taper adjustment may be accomplished by normalizing an IMT measurement based on a compiled database of IMT measurements relating the amount of taper with respect to location to characteristic IMT values.

41 Claims, 28 Drawing Sheets

U.S. PATENT DOCUMENTS

| | | | |
|---|---|---|---|
| 6,048,313 A | 4/2000 | Stonger | 600/443 |
| 6,048,314 A | 4/2000 | Nikom | 600/443 |
| 6,120,445 A * | 9/2000 | Grunwald | 600/437 |
| 6,132,373 A | 10/2000 | Ito et al. | 600/437 |
| 6,165,128 A * | 12/2000 | Cespedes et al. | 600/463 |
| 6,200,268 B1 * | 3/2001 | Vince et al. | 600/443 |
| 6,264,609 B1 | 7/2001 | Herrington et al. | 600/443 |
| 6,287,259 B1 * | 9/2001 | Grunwald | 600/437 |
| 6,301,498 B1 | 10/2001 | Greenberg et al. | 600/425 |
| 6,346,124 B1 | 2/2002 | Geiser et al. | 660/450 |
| 6,354,999 B1 | 3/2002 | Dgany et al. | 600/486 |
| 6,381,350 B1 | 4/2002 | Klingensmith et al. | 382/128 |
| 6,443,894 B1 | 9/2002 | Sumanaweera et al. | 600/443 |
| 6,450,964 B1 | 9/2002 | Webler | 600/467 |
| 6,514,202 B2 * | 2/2003 | Grunwald | 600/437 |
| 6,730,035 B2 * | 5/2004 | Stein | 600/449 |
| 2001/0009977 A1 | 7/2001 | Sato et al. | 600/441 |
| 2002/0086347 A1 | 7/2002 | Johnson et al. | 435/40.5 |
| 2002/0115931 A1 | 8/2002 | Strauss et al. | 600/420 |
| 2003/0199762 A1 | 10/2003 | Fritz et al. | 600/437 |
| 2004/0116813 A1 * | 6/2004 | Selzer et al. | 600/467 |
| 2004/0122326 A1 * | 6/2004 | Nair et al. | 600/467 |

* cited by examiner

ULTRASONIC BLOOD VESSEL MEASUREMENT APPARATUS AND METHOD

RELATED APPLICATIONS

This patent application claims the benefit of U.S. provisional patent applications Ser. No. 60/424,027 filed Nov. 6, 2002 and entitled METHOD AND APPARATUS FOR INTIMA-MEDIA THICKNESS MEASURING MECHANISM EMBEDDED IN ULTRASOUND IMAGING DEVICE; Ser. No. 60/424,464 filed Nov. 8, 2002 and entitled METHOD AND APPARATUS FOR MEASURING INTIMA-MEDIA THICKNESS ACROSS MULTIPLE SIMILAR IMAGES; Ser. No. 60/424,471 filed Nov. 8, 2002 and entitled METHOD AND APPARATUS FOR INCORPORATING INTIMA-MEDIA TAPERING EFFECTS ON INTIMA-MEDIA THICKNESS CALCULATIONS; Ser. No. 60/424,463 filed Nov. 8, 2002 and entitled METHOD AND APPARATUS FOR USING ULTRASOUND IMAGES TO CHARACTERIZE ARTERIAL WALL TISSUE COMPOSITION; and Ser. No. 60/424,465 filed Nov. 8, 2002 and entitled METHOD AND APPARATUS FOR REGENERATION OF INTIMA-MEDIA THICKNESS MEASUREMENTS. This application is also a continuation-in-part of U.S. patent application Ser. No. 10/407,682 filed Apr. 7, 2003 and entitled METHOD, APPARATUS, AND PRODUCT FOR ACCURATELY DETERMINING THE INTIMA-MEDIA THICKNESS OF A BLOOD VESSEL, now pending.

BACKGROUND

1. The Field of the Invention

This invention pertains to methods and apparatus for processing digital images of vascular structures including blood vessels. More particularly, it relates to methods for interpreting ultrasonic images of the common carotid artery.

2. The Background Art

Coronary artery disease (CAD) is a narrowing of the arteries that supply the heart with blood carrying oxygen and nutrients. CAD may cause shortness of breath, angina, or even heart attack. The narrowing of the arteries is typically due to the buildup of plaque, or, in other words, an increase in the atherosclerotic burden. The buildup of plaque may also create a risk of stroke, heart attacks, and embolisms caused by fragments of plaque detaching from the artery wall and occluding smaller blood vessels. The risk of plaque detachment is particularly great when it is first deposited on the artery wall inasmuch as it is soft and easily fragmented at that stage.

Measurement of the atherosclerotic burden of the coronary artery itself is difficult and invasive. Moreover, assessment of risk often involves measuring both the atherosclerotic burden and its rate of progression. This assessment therefore involves multiple invasive procedures over time. Treatment of CAD also requires additional invasive procedures to measure a treatment's effectiveness.

The carotid artery, located in the neck close to the skin, has been shown to mirror the atherosclerotic burden of the coronary artery. Moreover, studies have shown that a reduction of the atherosclerotic burden of the coronary artery will parallel a similar reduction in the carotid artery.

One noninvasive method for measuring the atherosclerotic burden is the analysis of ultrasound images of the carotid artery. High resolution, B-mode ultrasonography is one adequate method of generating such images. Ultrasound images typically provide a digital image of the various layers comprising the carotid artery wall, which may then be measured to determine or estimate the extent of atherosclerosis. Other imaging systems may likewise provide digital images of the carotid artery, such as magnetic resonance imaging (MRI) and radio frequency imaging.

The wall of the carotid artery comprises the intima, which is closest to the blood flow and which thickens, or appears to thicken, with the deposit of fatty material and plaque; the media, which lies adjacent the intima and which thickens as a result of hypertension; and the adventitia, which provides structural support for the artery wall. The channel in which blood flows is the lumen. The combined thickness of the intima and media layers, or intima-media thickness (IMT), is reflective of the condition of the artery and can accurately identify or reflect early stages of atherosclerotic disease.

An ultrasound image typically comprises an array of pixels, each with a specific value corresponding to its intensity. The intensity (brightness) of a pixel corresponds to the density of the tissue it represents, with brighter pixels representing denser tissue. Different types of tissue, each with a different density, are therefore distinguishable in an ultrasonic image. The lumen, intima, media and adventitia may be identified in an ultrasound image due to their differing densities.

An ultrasound image is typically formed by emitting sound waves toward the tissue to be measured and measuring the intensity and phase of sound waves reflected from the tissue. This method of forming images is subject to limitations and errors. For example, images may be subject to noise from imperfect sensors. Another source of error is the attenuation of sound waves that reflect off tissue located deep within the body or beneath denser tissue. Random reflections from various objects or tissue boundaries, particularly due to the non-planar ultrasonic wave, may add noise also.

The limitations of ultrasonography complicate the interpretation of ultrasound images. Other systems designed to calculate IMT thickness reject accurate portions of the image when compensating for these limitations. Some IMT measurement systems will divide an image into columns and examine each column, looking for maxima, minima, or constant portions of the image in order to locate the layers of tissue comprising the artery wall. Such systems may reject an entire column of image data in which selected portions of the wall are not readily identifiable. This method fails to take advantage of other portions of the artery wall that are recognizable in the column. Furthermore, examining columns of pixels singly fails to take advantage of accurate information in neighboring columns from which one may extrapolate, interpolate, or otherwise guide searches for information within a column of pixels.

Another limitation of prior methods is that they fail to adequately limit the range of pixels searched in a column of pixels. Noise and poor image quality can cause any search for maxima, minima, or intensity gradients to yield results that are clearly erroneous. Limiting the field of search is a form of filtering that eliminates results that cannot possibly be accurate. Prior methods either do not limit the field searched for critical points or apply fixed constraints that are not customized, or even perhaps relevant, to the context of the image being analyzed.

What is needed is a method for measuring the IMT that compensates for limitations in ultrasonic imaging methods. It would be an advancement in the art to provide an IMT measurement method that compensates for noise and poor image quality while taking advantage of accurate information within each column of pixels. It would be a further advancement to provide a method for measuring the IMT that limited the field of search for critical points to regions where the actual tissue or tissue boundaries can possibly be located.

BRIEF SUMMARY AND OBJECTS OF THE INVENTION

In view of the foregoing, it is a primary object of the present invention to provide a novel method and apparatus for extracting IMT measurements from ultrasound images of the carotid artery.

It is another object of the present invention to reduce error in IMT measurements by restricting searches for the lumen/intima boundary and media/adventitia boundary to regions likely to contain them.

It is another object of the present invention to bound a search region using a datum, or datums, calculated beforehand based on analysis of a large portion of a measurement region in order to improve processing speed and accuracy.

It is another object of the present invention to validate putative boundary locations using thresholds reflecting the actual make-up of the image.

It is another object of the present invention to validate putative boundary locations based on their proximity to known features of ultrasound images of the carotid artery.

It is another object of the present invention to compensate for sloping and tapering of the carotid artery as well as misalignment of an image frame of reference with respect to the axial orientation of the artery.

It is another object of the present invention to compensate for low contrast and noise by extrapolating and interpolating from high contrast portions of an image into low contrast portions of the image.

Consistent with the foregoing objects, and in accordance with the invention as embodied and broadly described herein, an apparatus is disclosed in one embodiment of the present invention as including a computer programmed to run an image processing application and to receive ultrasound images of the common carotid artery.

An image processing application may carry out a process for measuring the intima-media thickness (IMT) providing better measurements, less requirement for user skill, and a higher reproducibility. As a practical matter, intensity varies with the constitution of particular tissues. However, maximum difference in intensity is not typically sufficient to locate the boundaries of anatomical features. Accordingly, it has been found that in applying various techniques of curve fitting analysis and signal processing, structural boundaries may be clearly defined, even in the face of comparatively "noisy" data.

In certain embodiments of a method and apparatus in accordance with the invention, an ultrasonic imaging device or other imaging devices, such as a magnetic resonance imaging system (MRI), a computed tomography scan (CT-Scan), a radio frequency image, or other mechanism may be used to create a digital image. Typically, the digital image contains various pixels, each pixel representing a picture element of a specific location in the image. Each pixel is recorded with a degree of intensity. Typical intensity ranges run through values between zero and 255. In alternative embodiments, pixels may have color and intensity.

In certain embodiments, an image is first calibrated for dimensions. That is, to determine an IMT value, the dimensions of the image must necessarily be calibrated against a reference measurement. Accordingly, the scale on an image may be applied to show two dimensional measurements across the image.

In certain embodiments, an ultrasonic image is made with a patient lying on the back with the image taken in a horizontal direction. Accordingly, the longitudinal direction of the image is typically horizontal, and coincides with approximately the axial direction of the carotid artery. A vertical direction in the image corresponds to the approximate direction across the carotid artery.

In certain embodiments of methods and apparatus in accordance with the invention, a measurement region may be selected by a user, or by an automated algorithm. A user familiar with the appearance of a computerized image from an ultrasound system may quickly select a measurement region. For example, the horizontal center of an image may be selected near the media/adventitia boundary of the blood vessel in question.

Less dense materials tend to appear darker in ultrasound images, having absorbed the ultrasonic signal from a transmitter, and thus provide less of a return reflection to a sensor. Accordingly, a user may comparatively quickly identify high intensity regions representing the more dense and reflective material in the region of the adventitia and the darker, low density or absorptive region in the area of the lumen.

In general, a method or characterizing plaque buildup in a blood vessel may include a measurement of an apparent intima-media thickness. In one embodiment, the method may include providing an image. An image is typically oriented with a longitudinal direction extending horizontally relative to a viewer and a transverse direction extending vertically relative to a viewer. This orientation corresponds to an image taken of a carotid artery in the neck of the user lying on an examination table. Thus, the carotid artery is substantially horizontally oriented. The axial direction is the direction of blood flow in a blood vessel, and the lateral direction is substantially orthogonal thereto. The image is typically comprised of pixels. Each pixel has a corresponding intensity associated with the intensity of the sound waves reflected from that location of the subject represented by a selected region of the image created by the received waves at the wave receiver.

In selected embodiments of an apparatus and method in accordance with the invention, a series of longitudinal positions along the image may be selected and the brightest pixel occurring in a search in the lateral direction is identified for each longitudinal position. The brightest pixel at any longitudinal position is that pixel, located in a lateral traverse of pixels in the image, at which the image has the highest level of intensity. The brightest pixels may be curve fit by a curve having a domain along the longitudinal direction, typically comprising the longitudinal locations or positions, and having a range corresponding to the lateral locations of each of the brightest pixels. A curve fit of these brightest pixels provides a curve constituting an adventitia datum.

The adventitia datum is useful, although it is not necessarily the center, nor a boundary, of the adventitia. Nevertheless, a polynomial, exponential, or any other suitable mathematical function may be used to fit the lateral locations of pixels. The curve fit may also be accomplished by a piecewise fitting of the brightest pixel positions distributed along the longitudinal direction. Other curve fits may be made over the same domain using some other criterion for selecting the pixels in the range of the curve. In some embodiments, a first, second, or third order polynomial may be selected to piecewise curve fit the adventitia datum along segments of the longitudinal extent of the image. Other functions may be used for piecewise or other curve fits of pixels meeting selected criteria over the domain of interest.

In certain embodiments, a lumen datum may be located by one of several methods. In one embodiment, the lumen datum is found by translating the adventitia datum to a location in the lumen at which substantially every pixel along the curve shape has an intensity less than some threshold value. The threshold value may be a lowest intensity of the image. Alternatively, a threshold value may be something above the lowest intensity of pixels in the image, but nevertheless corresponding to the general regional intensity or a bounding limit thereof found within or near the lumen. The lowest intensity of the image may be extracted from a histogram of pixel intensities within a measurement region. In some embodiments, the threshold is set as the intensity of the lowest intensity pixel in the measurement region plus 10 percent of the difference in intensities between the highest and lowest intensities found in the measurement region. In still other embodiments, an operator may simply specify a threshold.

In another embodiment, the lumen datum may be identified by locating the pixel having a lowest intensity proximate some threshold value or below some threshold value. This may be further limited to a circumstance where the next several pixels transversely are likewise of such low intensity in a lateral (vertical, transverse) direction away from the adventitia. By whichever means it is found, a lumen datum comprises a curve fit of pixels representing a set of pixels corresponding to some substantially minimal intensity according to a bounding condition.

In certain embodiments, a media datum may be defined or located by fitting yet another curve to the lateral position of media dark pixels distributed in a longitudinal direction, substantially between the lumen datum and the adventitia datum. Media dark pixels have been found to evidence a local minimal intensity in a sequential search of pixels in a lateral direction, between the lumen datum and the adventitia datum. That is, image intensity tends to increase initially with distance from the lumen, then it tends to decrease to a local minimum within the media, then it tends to increase again as one moves from the media toward the adventitia.

As a practical matter, threshold values of intensity or distance may be provided to limit ranges of interest for any search or other operation using image data. For example, it has been found that a threshold value of ten percent of the difference, between the maximum intensity in a measurement region and the minimum intensity, added to the minimum intensity is a good minimum threshold value for assuring that media dark pixels found are not actually located too close to the lumen. Similarly, a threshold may be set below the maximum intensity within the measurement region, in order to assure that minima are ignored that may still be within the region of non-interest near the adventitia when searching for the location of media dark pixels. In some instances, 25 percent of the difference between maximum and minimum intensities added to the minimum intensity is a good increment for creating a threshold value.

In some circumstances, a pixel located within or at half the distance between (from) the adventitia datum and (to) the lumen datum may be used as the location of a media dark pixel, such as a circumstance where no adequate local minimum is found. That is, if the actual intensities are monotonically decreasing from the adventitia toward the lumen, then no local minimum may exist short of the lumen. In such a circumstance, limiting the media datum points considered to those closer to the adventitia than to the halfway point between the lumen datum and the adventitia datum has been shown to be an effective filter.

In general, the media datum is curve fit to the line of media dark pixels. However, it has also been found effective to establish a temporary curve fit of media dark pixels and move all media dark pixels lying between the temporary curve fit and the adventitia datum directly over (laterally) to the temporary curve fit. By contrast, those media dark pixels that may lie toward the lumen from the temporary curve fit are allowed to maintain their actual values. One physical justification for this filtering concept is the fact that the boundary of the adventitia is not nearly so subject to variation as the noise of data appears to show. Accordingly, and particularly since the actual media/adventitia boundary is of great importance, weighting the media datum to be fit to no points between the temporary curve fit and the adventitia datum, has been shown to be an effective filter.

In certain embodiments, the lumen/intima boundary may be determined by locating the largest local intensity gradient, that is, locating the maximum rate of change in intensity with respect to movement or position in the lateral direction in a traverse from the lumen datum toward the media datum. This point of local steepest ascent in such a lateral traverse has been found to accurately represent the lumen/intima boundary. A spike removing operation may be applied to a lumen/intima boundary to remove aberrant spikes in the boundary. The resulting boundary may also be curve fit to reduce error. In some embodiments the a spike removing operation is performed before any curve fit to improve the accuracy of the resulting curve.

Similarly, the media/adventitia boundary has been found to be accurately represented by those points or pixels representing the point of steepest ascent in intensity or most rapid change in intensity with respect to a lateral position, in a traverse from the media datum toward the adventitia datum. Clearly, the distance between the lumen/intima boundary and the media/adventitia boundary represents the intima-media thickness. A spike removing operation may be applied to a media/adventitia boundary to remove aberrant spikes in the boundary. The resulting boundary may also be curve fit to reduce error. In some embodiments the a spike removing operation is performed before any curve fit to improve the accuracy of the resulting curve.

BRIEF DESCRIPTION OF THE DRAWINGS

The foregoing and other objects and features of the present invention will become more fully apparent from the following description, taken in conjunction with the accompanying drawings. Understanding that these drawings depict only typical embodiments of the invention and are, therefore, not to be considered limiting of its scope, the invention may be seen in additional specificity and detail in the accompanying drawings where.

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1–29, is not intended to limit the scope of the invention, as claimed, but is merely representative of certain presently preferred embodiments in accordance with the invention. These embodiments will be best understood by reference to the drawings, wherein like parts are designated by like numerals throughout.

Those of ordinary skill in the art will, of course, appreciate that various modifications to the details illustrated in FIGS. 1–29 may easily be made without departing from the essential characteristics of the invention. Thus, the following description is intended only by way of example, and simply illustrates certain presently preferred embodiments consistent with the invention as claimed herein.

Figure 1:
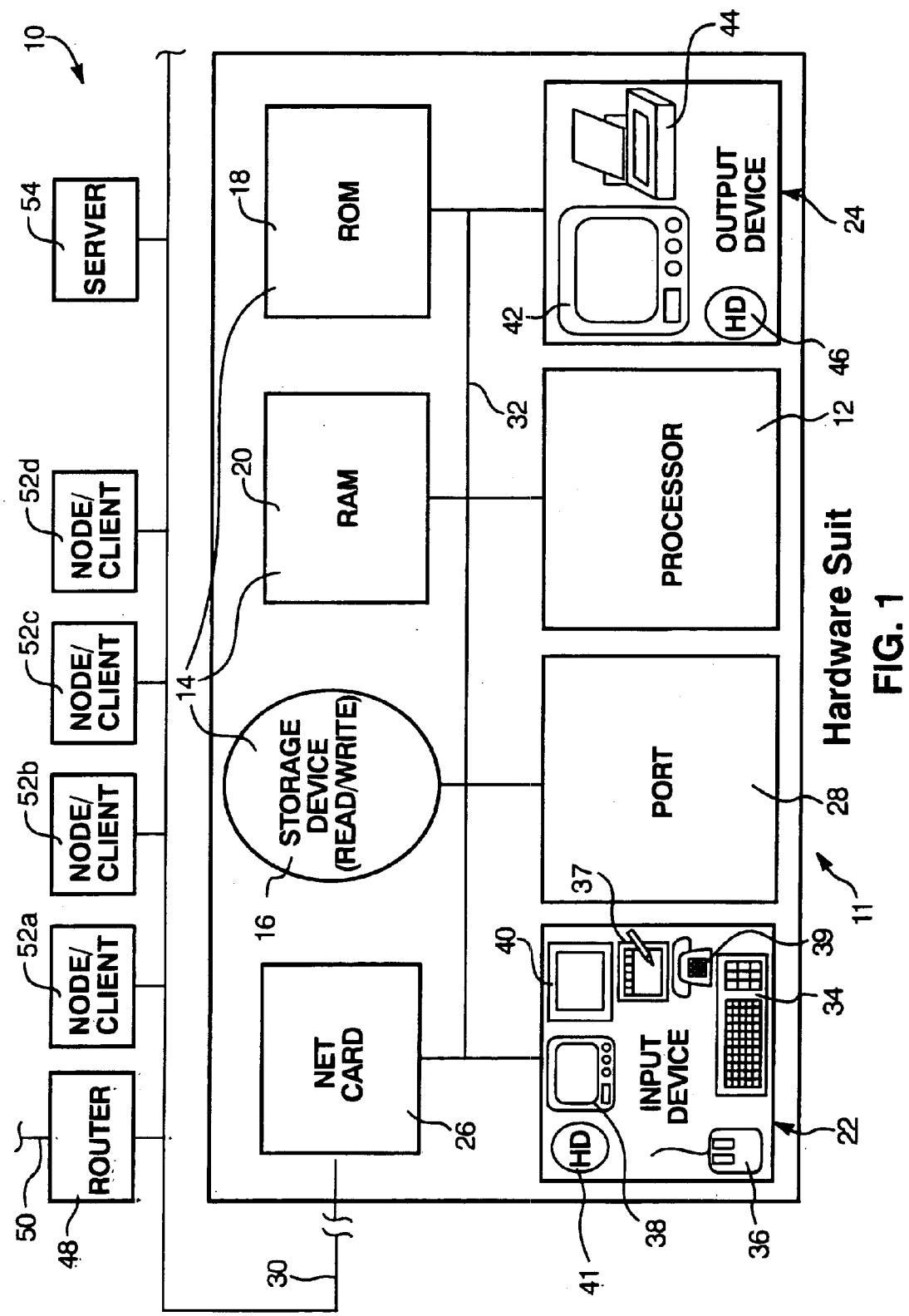
FIG. 1 is a schematic diagram of a general purpose computer suitable for use in accordance with the present invention.

Referring now to FIG. 1, an apparatus 10 may include a node 11 (client 11, computer 11) containing a processor 12 or CPU 12. The CPU 12 may be operably connected to a memory device 14. A memory device 14 may include one or more devices such as a hard drive 16 or non-volatile storage device 16, a read-only memory 18 (ROM) and a random-access (and usually volatile) memory 20 (RAM).

The apparatus 10 may include an input device 22 for receiving inputs from a user or another device. Similarly, an output device 24 may be provided within the node 11, or accessible within the apparatus 10. A network card 26 (interface card) or port 28 may be provided for connecting to outside devices, such as the network 30.

Internally, a bus 32 (system bus 32) may operably interconnect the processor 12, memory devices 14, input devices 22, output devices 24, network card 26 and port 28. The bus 32 may be thought of as a data carrier. As such, the bus 32 may be embodied in numerous configurations. Wire, fiber optic line, wireless electromagnetic communications by visible light, infrared, and radio frequencies may likewise be implemented as appropriate for the bus 32 and the network 30.

Input devices 22 may include one or more physical embodiments. For example, a keyboard 34 may be used for interaction with the user, as may a mouse 36. A touch screen 38, a telephone 39, or simply a telephone line 39, may be used for communication with other devices, with a user, or the like.

Similarly, a scanner 40 may be used to receive graphical inputs which may or may not be translated to other character formats. A hard drive 41 or other memory device 14 may be used as an input device whether resident within the node 11 or some other node 52 (e.g., 52a, 52b, etc.) on the network 30, or from another network 50.

Output devices 24 may likewise include one or more physical hardware units. For example, in general, the port 28 may be used to accept inputs and send outputs from the node 11. Nevertheless, a monitor 42 may provide outputs to a user for feedback during a process, or for assisting two-way communication between the processor 12 and a user. A printer 44 or a hard drive 46 may be used for outputting information as output devices 24.

In general, a network 30 to which a node 11 connects may, in turn, be connected through a router 48 to another network 50. In general, two nodes 11, 52 may be on a network 30, adjoining networks 30, 50, or may be separated by multiple routers 48 and multiple networks 50 as individual nodes 11, 52 on an internetwork. The individual nodes 52 may have various communication capabilities.

In certain embodiments, a minimum of logical capability may be available in any node 52. Note that any of the individual nodes 52, regardless of trailing reference letters, may be referred to, as may all together, as a node 52 or nodes 52.

A network 30 may include one or more servers 54. Servers may be used to manage, store, communicate, transfer, access, update, and the like, any number of files for a network 30. Typically, a server 54 may be accessed by all nodes 11, 52 on a network 30. Nevertheless, other special functions, including communications, applications, and the like may be implemented by an individual server 54 or multiple servers 54.

In general, a node 11 may need to communicate over a network 30 with a server 54, a router 48, or nodes 52. Similarly, a node 11 may need to communicate over another network (50) in an internetwork connection (e.g. Internet) with some remote node 52. Likewise, individual components of the apparatus 10 may need to communicate data with one another. A communication link may exist, in general, between any pair of devices or components.

By the expression "nodes" 52 is meant any one or all of the nodes 48, 52, 54, 56, 58, 60, 62, 11. Thus, any one of the nodes 52 may include any or all of the component parts illustrated in the node 11.

To support distributed processing, or access, a directory services node 60 may provide directory services as known in the art. Accordingly, a directory services node 60 may host software and data structures required for providing directory services to the nodes 52 in the network 30 and may do so for other nodes 52 in other networks 50.

The directory services node 60 may typically be a server 54 in a network. However, it may be installed in any node 52. To support directory services, a directory services node 52 may typically include a network card 26 for connecting to the network 30, a processor 12 for processing software commands in the directory services executables, a memory device 20 for operational memory as well as a non-volatile storage device 16 such as a hard drive 16. Typically, an input device 22 and an output device 24 are provided for user interaction with the directory services node 60.

Figure 2:
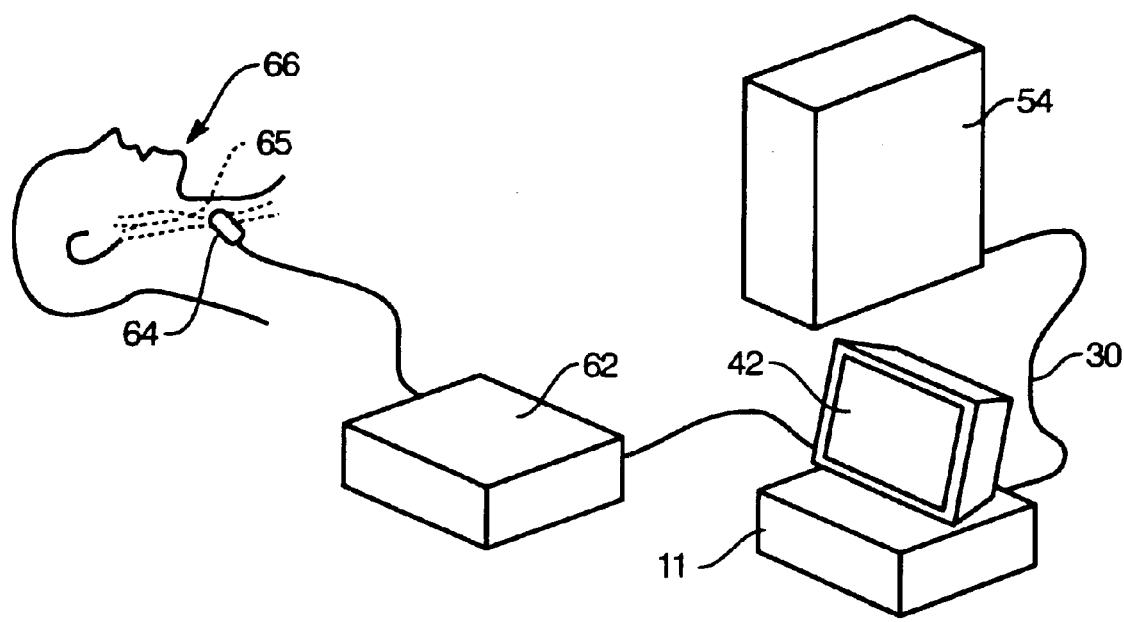
FIG. 2 is a schematic representation of a system suitable for creating and analyzing ultrasonic images of a carotid artery.

Referring to FIG. 2, in one embodiment, a node 11 may be embodied as any digital computer 11, such as a desktop computer 11. The node 11 may communicate with an ultrasound system 62 having a transducer 64, or "sound head" 64, for emitting sound waves toward tissue to be imaged and sensing sound waves reflected from the tissue. The ultrasound system 62 then interprets the reflected sound waves to form an image of the tissue. The image may then be transmitted to the node 11 for display on a monitor 42 and/or for analysis. The transducer 64 may be positioned proximate the carotid artery 65 located in the neck of a patient 66 in order to produce an ultrasonic image of the common carotid artery (herinafter "the carotid artery"). Of course, other imaging methods such as magnetic resonance imaging (MRI) or the like may be used to generate an image of a carotid artery 65.

A server 54 may be connected to the node 11 via a network 30. The server 54 may store the results of analysis and/or archive other data relevant to the measurement of the carotid artery and the diagnosis of medical conditions.

Figure 3:
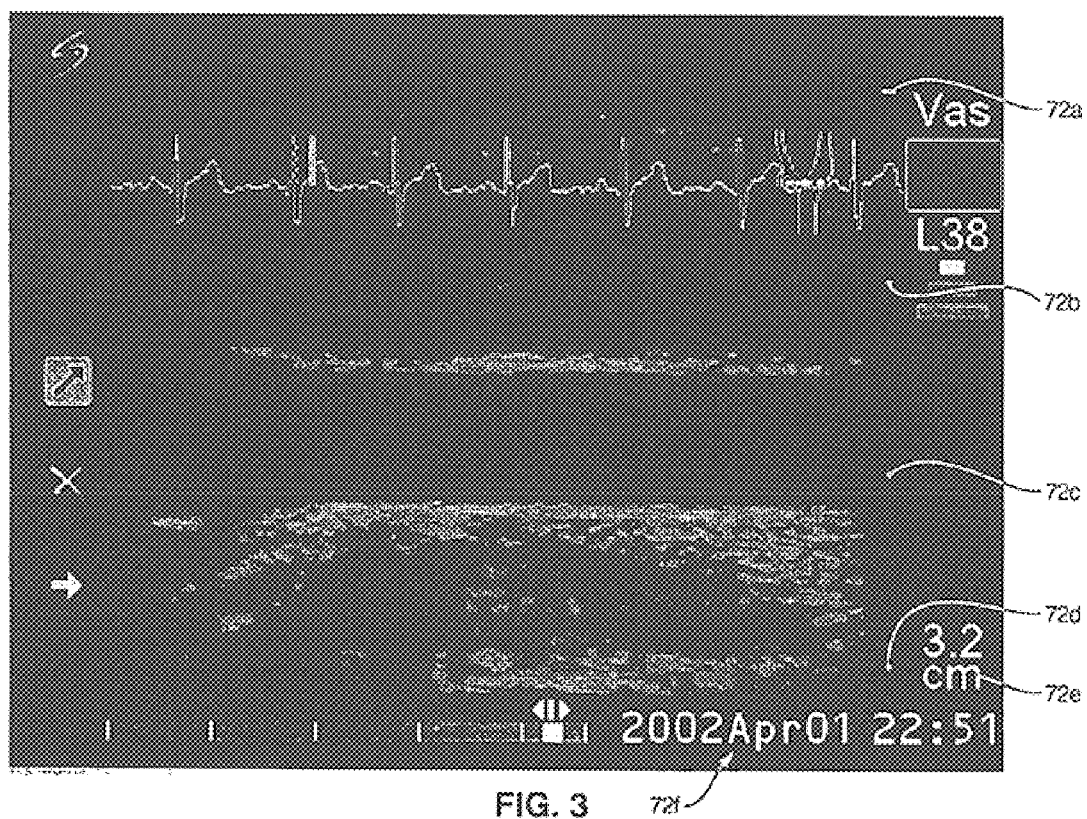
FIG. 3 is an example of an ultrasonic image of the common carotid artery.

FIG. 3 is an example of an ultrasonic image of a carotid artery produced by an ultrasound system 62. The shades of gray indicate reflectivity, and typically density, of the tissue, with white areas representing the densest and most reflective tissue and black areas the least dense or least reflective tissue. The image output by the ultrasound system may also include markings such as calibration marks 72a–72e or a time stamp 72f.

Figure 4:
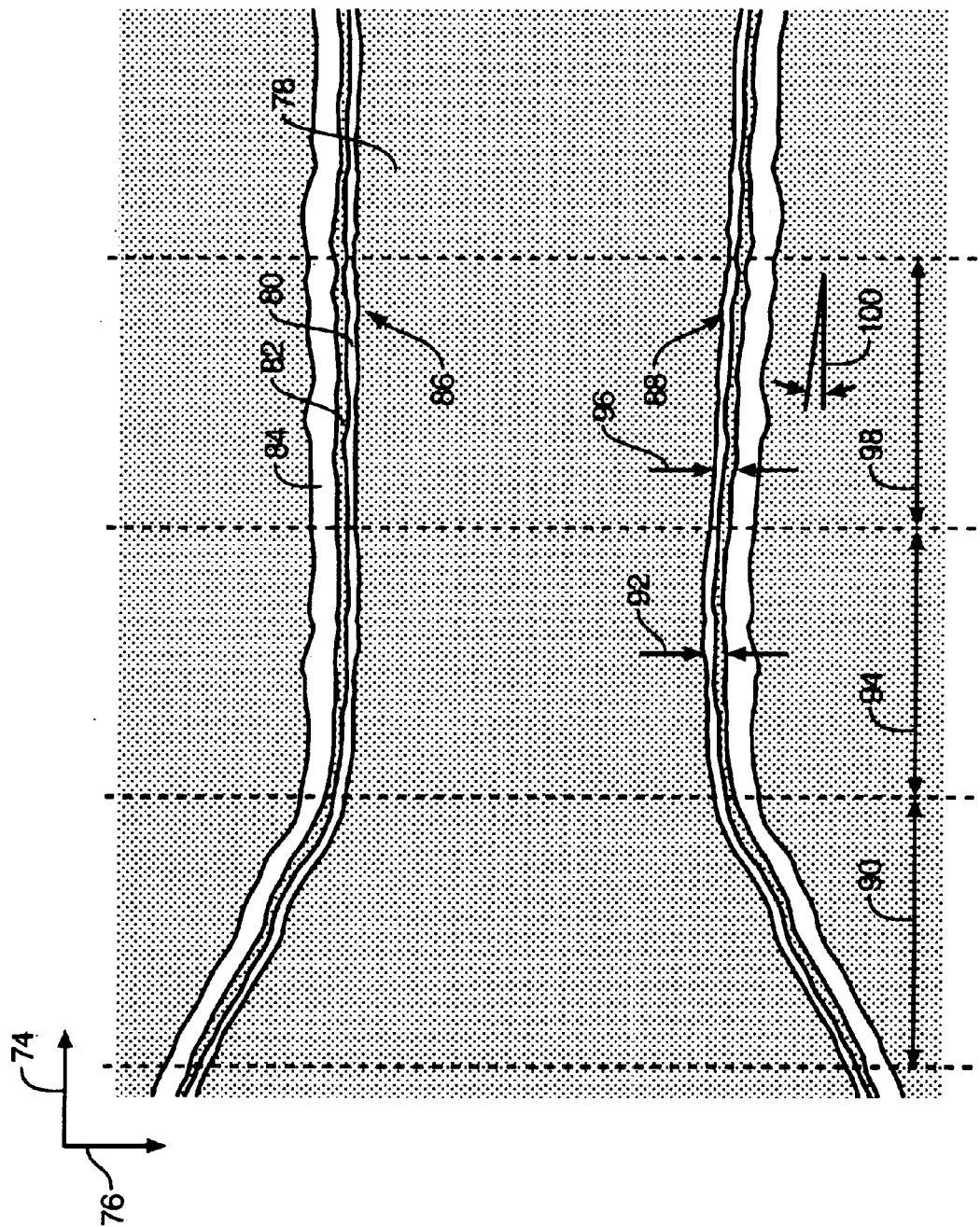
FIG. 4 is a simplified representation of certain features of an ultrasonic image of the common carotid artery.

Referring to FIG. 4, an ultrasonic image of the carotid artery comprises an array of pixels each associated with a numerical value representing the intensity (e.g. black, white, gray shade, etc.) of that pixel. Accordingly, a horizontal direction 74 may be defined as extending along the rows of pixels in the image and a lateral direction 76 may be defined as extending along the columns of pixels. In some embodiments of the invention, the lateral direction 76 may be substantially perpendicular to the direction of blood flow in the carotid artery. The horizontal direction 74 may be substantially parallel to the direction of blood flow.

An ultrasonic image of the carotid artery typically reveals various essential features of the artery, such as the lumen 78, representing the cavity portion of the artery wherein the blood flows, as well as the intima 80, the media 82, and the adventitia 84, all of which form the wall of the artery. The thickness of the intima 80 and the media 82 (intima-media thickness or IMT) may be measured to diagnose a patient's risk of arterial sclerosis such as coronary artery disease.

The image typically shows the near wall 86 and the far wall 88 of the artery. The near wall 86 being closest to the skin. The far wall 88 typically provides a clearer image inasmuch as the intima 80 and media 82 are less dense than the adventitia 84 and therefore interfere less with the sound waves reflected from the adventitia 84. To image the near wall 86, the sound waves reflected from the intima 80 and media 82 must pass through the denser adventitia 84, which interferes measurably with the sound waves.

As the common carotid artery extends toward the head it eventually bifurcates into the internal and external carotid arteries. Just before the bifurcation, the common carotid artery has a dilation point 90. The IMT 92 of the approximately 10 mm segment 94 below this dilation point 90 (the portion of the common carotid artery distal from the heart) is typically greater than the IMT 96 of the segment 98 extending between 10 mm and 20 mm away from the dilation point 90 (the portion of the common carotid artery proximate the heart). This is the case 88% of the time in the younger population (average age 25), with the IMT 92 of the segment 94 being 14% thicker than the IMT 96 of the segment 98. On the other hand, 12% of the time the IMT 92 may be the same as the IMT 96, or thinner. Among the older population (average age 55), the IMT 92 is 8% greater than the IMT 96 in 69% of the population. However, in 31% of the older population, the IMT 92 is the same as or smaller than the IMT 96.

This tapering of the IMT as one moves away from the bifurcation may introduce uncertainty into the interpretation of an IMT measurement, inasmuch as variation in IMT measurements may simply be due to shifting the point at which a measurement was taken. Furthermore, the walls 86,88 may be at an angle 100 relative to the horizontal direction 74, Therefore, IMT measurements that analyze lateral columns of pixels may vary due to the orientation of the carotid artery in the image rather than actual variation in thickness.

Figure 5:
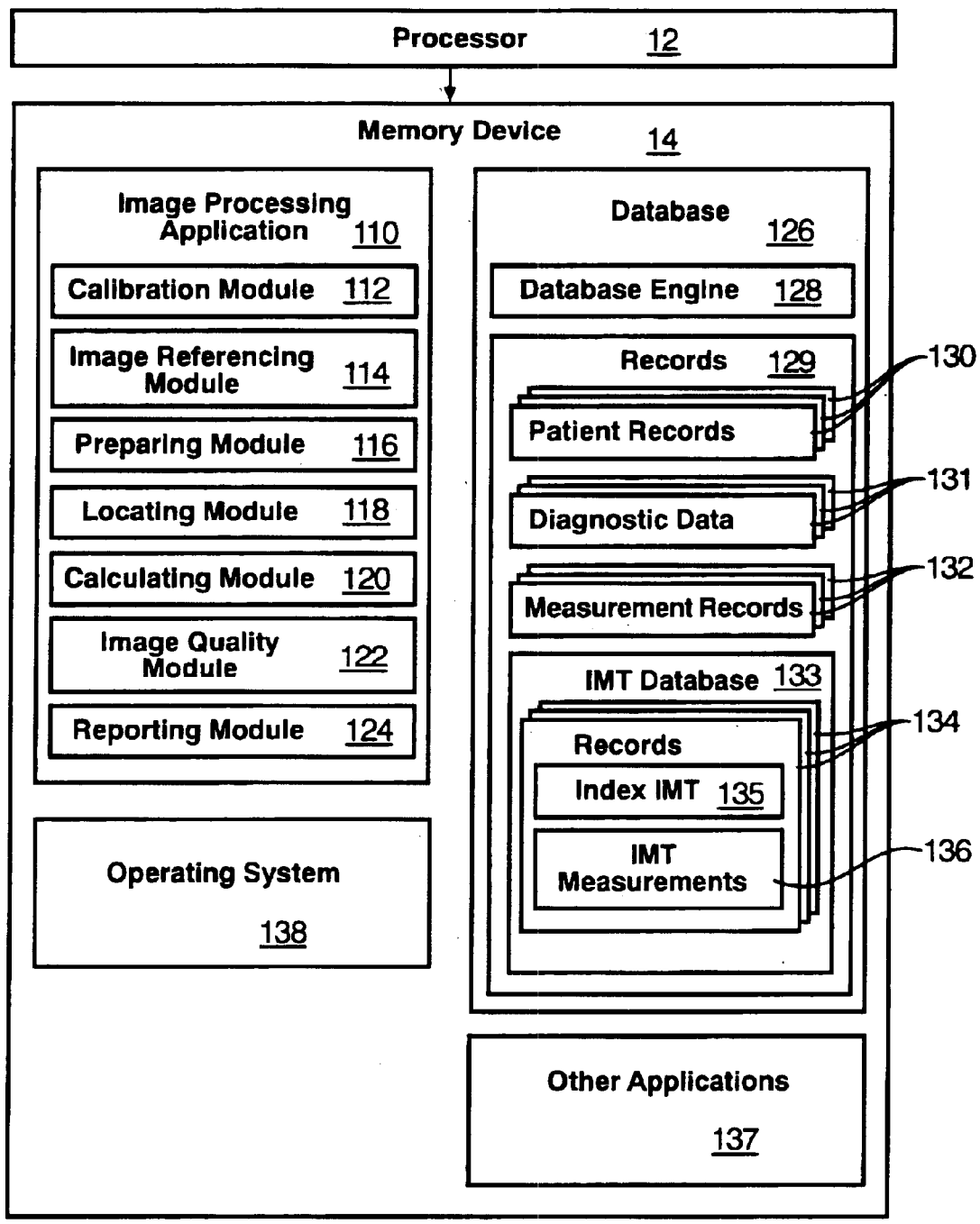
FIG. 5 is a schematic block diagram of a computing system and data structures suitable for analyzing ultrasonic images, in accordance with the invention.

Referring to FIG. 5, a memory device 14 coupled to a processor 12 may contain an image processing application 110 having executable and operational data structures suitable for measuring, among other things, the IMT of the carotid artery. The image processing application may include a calibration module 112, an image referencing module 114, a preparing module 116, a locating module 118, a calculating module 120, an image quality module 122, and a reporting module 124.

The calibration module 112 may correlate the distances measured on the image to real world distances. The calibration module 112 typically takes as inputs the pixel coordinates of two points in an image as well as the actual distance between the points. The calibration module then uses these known values to convert other distances measured in the image to their true values.

The calibration module 112 may extract the pixel coordinates from the image by looking for the calibration marks 72*a*–72*e*. The true distance between the marks 72*a*–72*d* may be known such that no user intervention is needed to provide it, or the calibration module may prompt a user to input the distance or extract the value from a file or the like. Alternatively mark 72*e* may indicate this distance between the calibration points 72*a*–72*d* In some embodiments, such information as the model of ultrasound machine 62, zoom mode, or the like may be displayed, and the calibration module 112 may store calibration factors and the like mapped to the various ultrasound machines 62 and their various zoom modes. The calibration module may then calibrate an image based on known calibration factors for a particular ultrasound machine 62 in a particular zoom mode. The calibration module 112 may also search for "landmarks," such as physical features, patterns, or structures, in an image and perform the calibration based on a known distance between the landmarks or a known size of a landmark.

The image referencing module 114, preparing module 116, locating module 118, and calculating module 120 typically interpret the image and extract IMT measurements and the like. The operation of these modules will be described in greater detail below.

The image quality module 122 may operate on the image, or a selected region of interest within an image, to remove noise and otherwise improve the image. For example, the image quality module 122 may apply a low pass filter to remove noise from the image or use an edge detection or embossing filter to highlight edges. In a typical ultrasound image of the carotid artery, the layers of tissue extend parallel to the horizontal direction 74. Accordingly, a lateral filter may be applied in a substantially horizontal direction 74, or a direction parallel to the boundary between the layers of tissue, to reduce noise in a biased direction, to prevent loss of edge data that may indicate the boundary between different layers of tissue.

The image quality module 122 may also notify a user when an image is too noisy to be useful. For example, the image quality module may display on a monitor 42 a gauge, such as a dial indicator, numerical value, color coded indicator, or the like, indicating the quality of the image. In some embodiments, the image quality module 122 may evaluate the quality of an image by first locating the portion of the image representing the lumen 78. Because the lumen 78 is filled with blood of substantially constant density, a high quality image of the lumen would be of substantially constant pixel intensity. Accordingly, the image quality module 122 may calculate and display the standard deviation of pixel intensities within the lumen as an indicator of the noisiness of an image. The smaller the standard deviation of the pixel intensities, the higher the quality of the image.

The image quality module 122 may locate the lumen 78 in the same manner as the locating module 118 as discussed below. After finding the lumen/intima boundary at both the near wall 86 and the far wall 88, the image quality module 122 may examine the region between the two boundaries to calculate the standard deviation of lumen pixel intensities. Alternatively, the image quality module 122 may evaluate a region of predetermined dimensions with one edge lying near the lumen/intima boundary.

Another criterion that the image quality module 122 may use to evaluate quality is a histogram of pixel intensities in a measurement region or, in other words, a portion of the image where the IMT is measured. Alternatively, a larger area including the area surrounding the measurement region may be used to compute the histogram. The form of the histogram will typically vary in accordance with the quality of the image. The image quality module 122 may store an image of a histogram generated from a high quality image and display it on an output device 24 along with the histogram of the image being analyzed.

Operators may then be trained to identify a "good" histogram in order to determine whether measurements taken from a particular image are reliable. The image quality module 122 may likewise store and display images of medium quality and poor quality histograms to aid an operator. Alternatively, the image quality module 122 may automatically compare a histogram to stored images high, medium, and/or low quality histograms and rate their similarity. This may be accomplished by pattern-matching techniques or the like.

The reporting module 124 may format the results of calculations and send them to an output device 24, such as a monitor 42, printer 44, hard drive 46, or the like. The image processing application 110 may also store results in, or retrieve information from, a database 126 having a database engine 128 for storing, organizing, and retrieving archived data. The database 126, as with any module comprising the invention, may be physically located on the same node 11 or may be located on a server 54, or other node 52*a*–52*d,* and may communicate with a node 11 via a network 30. The database engine 128 may be that of any suitable databasing application known in the art.

The database 126 may store various records 129. The records 129 may include patient records 130. Patient records 130 may store such information as a patient's age, weight, risk factors, cardiovascular diseases, prior IMT measurements, and other relevant medical information. The diagnostic data 131 may provide data to support a statistical analysis of a patient's risk of developing a cardiovascular disease. For example, diagnostic data 131 may include the results of studies, or the like, linking IMT measurements and/or other risk factors with a patient's likelihood of developing coronary artery disease.

Measurement records 132 may include information concerning the measurement process itself. For example, measurement records 132 may include a reference to an ultrasound image analyzed or the image itself. Measurement records 132 may also include any inputs to the measurement process, the name of the operator who performed the measurement, the algorithm used to analyze the image, values of various parameters employed, the date the measurement was made, ultrasound machine data, values of sources of error, and the like.

The IMT database 133 may archive IMT measurements for use in the interpretation of later ultrasound images. The IMT database 133 may include records 134 of prior measurements, each including an index IMT 135. The index IMT 135 may be an IMT value used to characterize the record 134. For example, IMT measurements along a portion of the carotid artery may be stored based on the IMT at a standardized point on an individual carotid artery. Accordingly, the index IMT 135 may be the IMT at the standardized point. Alternatively, the average of all IMT measurements along the portion measured may be used as the index IMT 135. IMT measurements 136 may include IMT measurements made at various points along the length of the carotid artery. The IMT measurements 136 may be of one ultrasound image, or an average of measurements from multiple ultrasound images. In some embodiments an IMT measurement 36 may be a polynomial curve fit of IMT measurements taken along a portion of an artery.

The memory device 14 may also contain other applications 137 as well as an operating system 138. The operating system 138 may include executable (e.g. programming) and operational (e.g. information) data structures for controlling the various components comprising the node 11. Furthermore, it will be understood that the architecture illustrated in FIGS. 2 and 5 is merely exemplary, and various other architectures are possible without departing from the essential nature of the invention. For example, a node 11 may simply be an ultrasound system 62 having at least a memory device 14 and a processor 12. Accordingly, the image processing application 110 and/or the database 126 may be embedded in the ultrasound system 62. An ultrasound 62 may also include a monitor 42, or other graphical display such as an LCD or LED, for presenting ultrasound images and the results of calculations.

Figure 6:
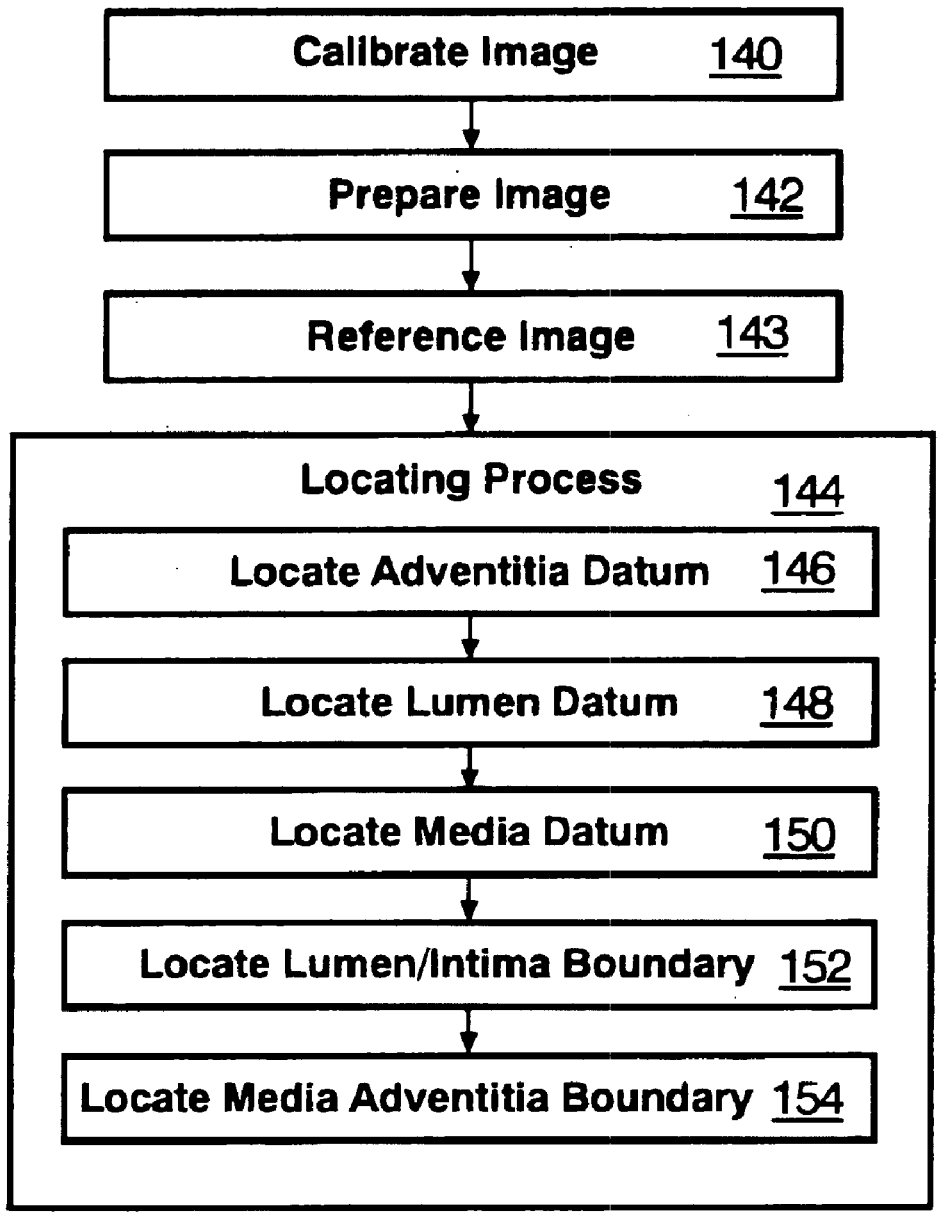
FIG. 6 is a process flow diagram of a process suitable for locating certain features in an ultrasonic image of an artery, in accordance with the invention.

Referring to FIG. 6, the process of locating essential features of the carotid artery may include the illustrated steps. It will be understood that the inclusion of steps and the ordering of steps is merely illustrative and that other combinations and orderings of steps are possible without departing from the essential nature of the invention.

The process may include an image calibration step 140 to perform the operations described above in conjunction with the calibration module 112. The preparing step 142 may identify the region of the image representing a portion of the near wall 86 or far wall 88 to be analyzed. The referencing step 143 may calculate thresholds, or other reference values, based on the image for use in later calculations.

The locating process 144 may identify the various layers of tissue forming the artery walls 86, 88. It may also locate the boundaries between the layers of tissue. Accordingly, the locating process may include an adventitia datum locating step 146, which identifies the location of the adventitia 84 and establishes a corresponding datum. The lumen datum locating step 148 may establish a datum curve within the lumen. The media datum locating step 150 may identify the portion of the artery wall corresponding to the media and establish a corresponding datum. The lumen/intima boundary locating step 152 may search between the lumen datum and the media datum for the lumen/intima boundary. The media/adventitia boundary locating step 154 may search between the media datum and the adventitia datum for the media/adventitia boundary.

Figure 7:
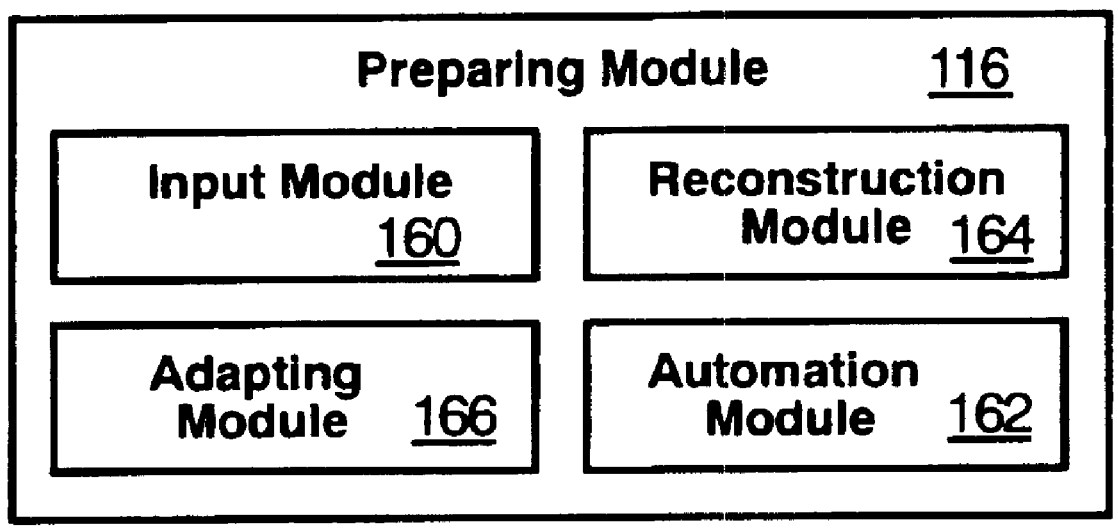
FIG. 7 is a schematic block diagram of data structures suitable for implementing a preparing module in accordance with the invention.

Referring to FIG. 7, modules are executables, programmed to run on a processor 12, and may be stored in a memory device 14. The preparing step 142 may be carried out by the preparing module 116, which may comprise an input module 160, an automation module 162, a reconstruction module 164, and an adapting module 166.

Figure 8:
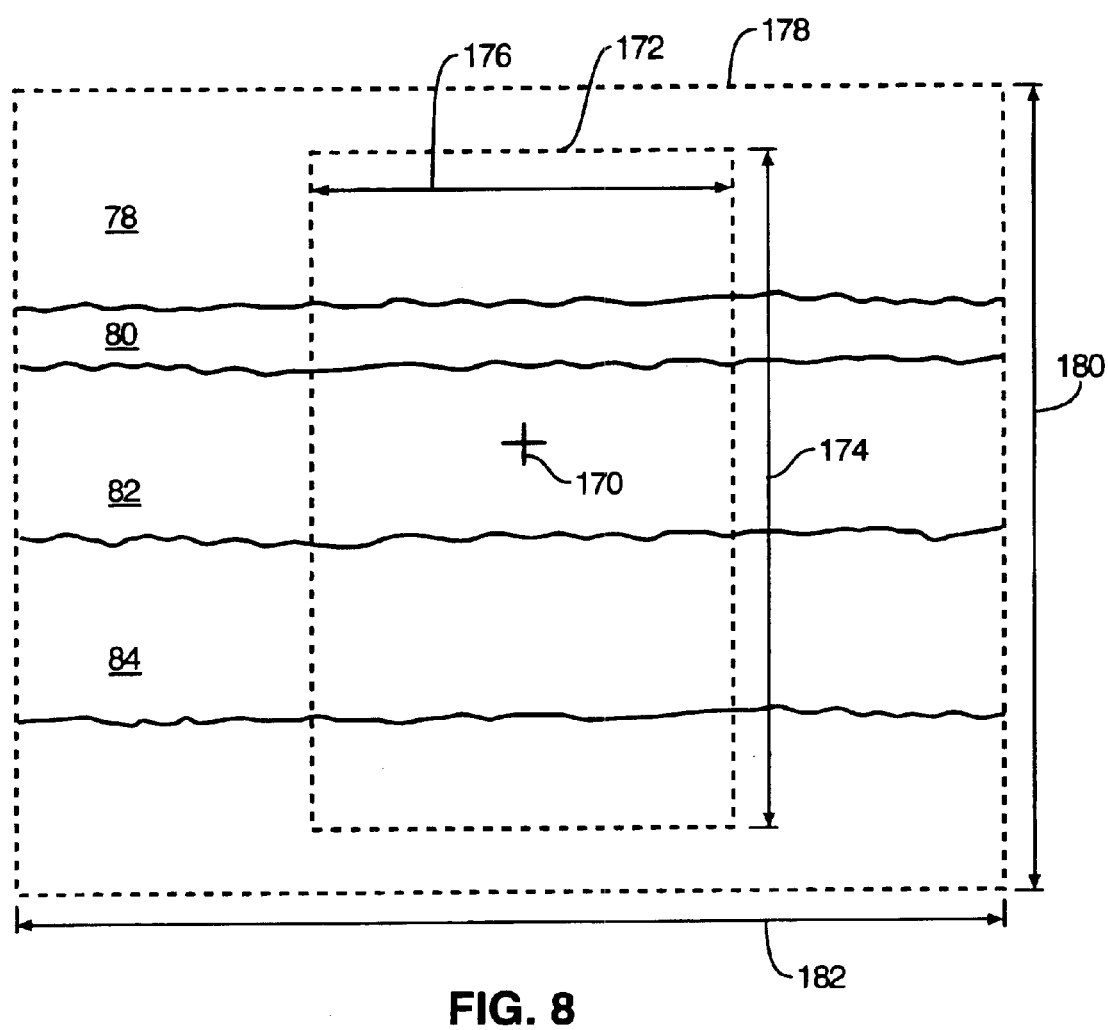
FIG. 8 is a schematic representation of a measurement region and a sampling region superimposed on an ultrasound image of the wall of an artery, in accordance with the invention.

Referring to FIG. 8, the input module 160 may permit a user to select a point 170 in an image, which will serve as the center of a measurement region 172. The IMT of columns of pixels within the measurement region may be measured and all columns averaged together, or otherwise combined, to yield a final IMT measurement and other information. Alternatively, the IMT can be curve fit longitudinally. Accordingly, the height 174 of the measurement region 172 may be chosen such that it includes at least portions of the lumen 78, the intima 80, the media 82, and the adventitia 84.

The input module 160 may enable a user to specify a width 176 of the measurement region 172. Alternatively, the input module 160 may simply use a predetermined value. For example, one adequate value is 5 mm, which is also approximately the diameter of the carotid artery in most cases. Whether found automatically, bounded automatically or by a user, or specified by a user, the width 176 may also be selected based on the image quality. Where the image is noisy or has poor contrast, a larger width 176 may be used to average out errors. In embodiments where the width 176 is chosen automatically, the input module 160 may choose the width based on an indicator of image quality calculated by the image quality module 122. Likewise, an operator may be trained to manually adjust the width 176 based on indicators of image quality output by the image quality module 122. In some embodiments, the input module may incrementally increase or decrease the width 176 in response to a user input such as a mouse click or keystroke.

The input module 160 may also determine which wall 86, 88 to measure by determining which wall 86, 88 is laterally nearest the point 170. This may be accomplished by finding the highly recognizable adventitia 84 in each wall 86, 88 and comparing their proximity to the point 170. Alternatively, the input module 160 may choose the wall 86, 88 having the highest (or highest average, highest mean, etc.) intensity in the adventitia 84, and which therefore has a greater likelihood of having desirable high contrast.

The point 170 may also serve as the center of a sampling region 178. The pixels bounded by the sampling region 178 are used to generate a histogram of pixel intensities that is used by other modules to determine certain threshold values and to evaluate the quality of the image. The height 180 is typically chosen to include a portion of both the lumen 78 and adventitia 84 inasmuch as these represent the lowest and highest intensity regions, respectively, of the image and will be relevant to analysis of the histogram. The width 182 may be chosen to provide an adequate sampling of pixel intensities. In some embodiments, the width 182 is simply the same as the width 176 of the measurement region 172. Adequate values for the height 180 have been shown to be from one-half to about one-fourth of the width 176 of the measurement region 172.

The automating or automation module 162 may automatically specify the location of a measurement region 172 and/or a sampling region 178. The automation module 162 may accomplish this by a variety of means. For example, the automation module may simply horizontally center the region 172 at the center of the image. The lateral center of the region 172 may be set to the location of the brightest pixels in the lateral column of pixels at the center of the image. These brightest pixels would correspond to the adventitia 84 of the wall having the highest, and therefore the best, contrast. Alternatively, the automation module 162 may located the lumen 78 by searching a central column of pixels for a large number of contiguous pixels whose intensity, or average intensity, is below a specific threshold corresponding to the intensity of pixels in the lumen. One side of this group of pixels may then be chosen as the center of the measurement region 172 inasmuch as the sides will have a high probability of being proximate the lumen/intima boundary. The automating module 162 may also adjust the size and location of the measurement region 172 and sampling region 178 to exclude marks 72a–72f that may be found in an image. The automating module 162 may also adjust a user selected measurement region 172 and sampling region 178 to avoid such marks 72a–72f.

Referring again to FIG. 7, the reconstruction module 164 may store relevant user inputs, such as the location of the point 170 or any user specified dimensions for the regions 172, 178 in the database 126. The reconstruction module 164 may also store a signature uniquely identifying the image measured, or may store the image itself. The reconstruction module 164 may also store other inputs such as the algorithm used to locate the layers of tissue or the method used to eliminate noise.

The reconstruction module 164 may store this information in any accessible storage location, such as in the database 126 as measurement data 132 or the hard drive 46 of the node 11. The reconstruction module 164 may then retrieve this information and use it to recreate an IMT measurement and its process of construction. The reconstruction module 164 may also allow a user to adjust the inputs prior to recreating a prior measurement. Therefore, one can readily study the effect a change of an individual input has on the measurement results.

The ability to retrieve inputs and to recreate an IMT measurement may be useful for training operators to use the image processing application 110. This ability enables an expert to review the measurement parameters specified by an operator and provide feedback. The inputs specified by an operator can also be stored over a period of time and used to identify trends or changes in an operator's specification of measurement parameters and ultimately allow for validation and verification of an operator's proficiency.

The adapting module 166 may adapt inputs and the results of analysis to subsequent images in order to reduce computation time. This is especially useful for tracking IMT values in a video clip of ultrasound images which comprises a series of images wherein the image before and the image after any given image will be similar to it. Given the similarity of the images, needed inputs and the results of analysis will typically not vary greatly between consecutive images.

For example, the adapting module 166 may adapt a user selected region 172, 178 to successive images. The results of other computations discussed below may also be stored by the adapting module 166 and reused. For example, the angle 100 and the location of adventitia, media, and lumen datums, provide rough but still usefully accurate estimates of the location of the boundaries between layers of tissue. The adapting module 166 may also use reference values, or thresholds, generated from the analysis of the histogram of a previous sampling region 178 for the measurement of a subsequent image.

Figure 9:
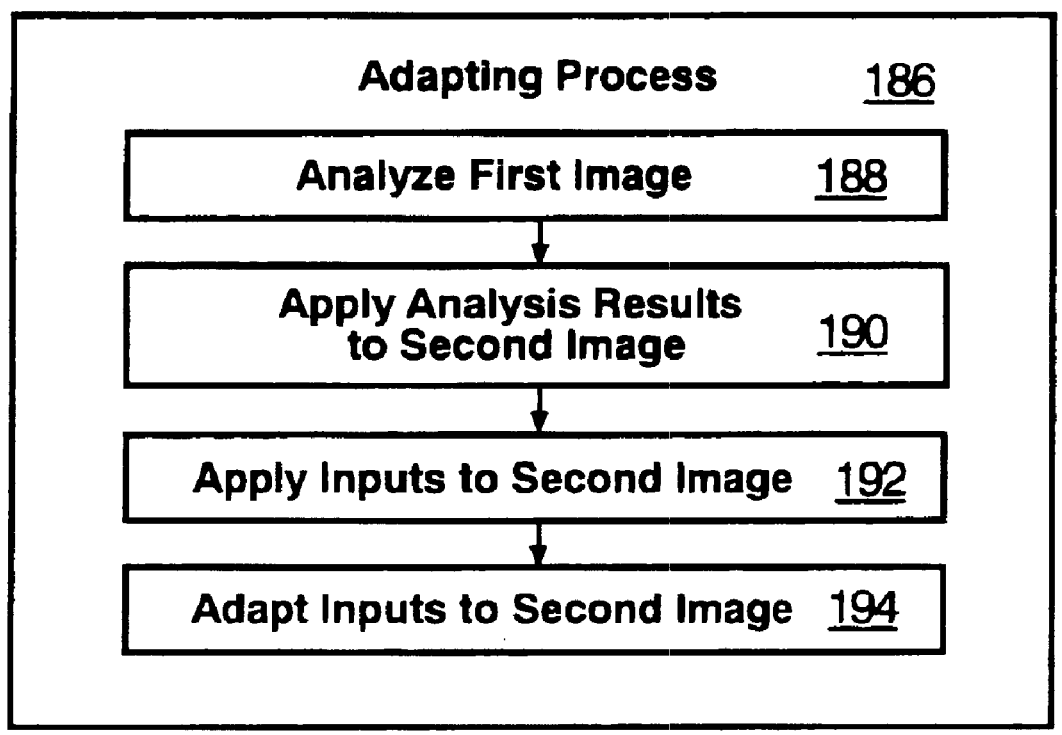
FIG. 9 is a process flow diagram of an adapting process, in accordance with the invention.

Referring to FIG. 9, the adapting module 166 may also adapt inputs, datums, and other results of calculations to accommodate change in the image. For example, the adapting module 166 may shift the location of the region 172 in accordance to shifting of the carotid artery between successive images due to movement of the artery itself or movement of the transducer 64. That is, the module 166 may re-register the image to realign object in the successive images of the same region.

Adapting the location of the regions 172, 178 may provide a variety of benefits, such as reducing the time spent manually selecting or automatically calculating a region 172, 178. The reduction in computation time may promote the ability to track the location of the layers of tissue in the carotid artery in real time. By reducing the time spent computing the regions 172, 178 the image processing application 110 can measure video images at higher frame rates without dropping or missing frames.

Accordingly, the adapting module 166 may carry out an adapting process 186 automatically or with a degree of human assistance or intervention. An analyzing step 188 is typically carried out by other modules. However, it is the first step in the adapting process 186. Analyzing 188 a first image may include calculating reference values for use in later calculations, in identifying lumen, adventitia, and lumen datums in the image or both. Analyzing 188 may also include locating the boundaries between layers of tissue.

Once a first image has been analyzed, applying 190 analysis results to a second image may include using one or more of the same lumen, adventitia, or media datum located in a first image in the analysis of the second image. Applying 190 results from a first image to a second may simply include using results without modification in the same manner as the results were used in the first image. For example, a datum calculated for a first image may be used without modification in a second. Alternatively, applying 190 may involve using the results as a rough estimate (guess) that is subsequently refined and modified during the measurement process.

For example, the adventitia 84 typically appears in ultrasound images as the brightest portion of the carotid artery. Accordingly, locating the adventitia may involve finding a maximum intensity (brightness) region. Once the adventitia 84 is located in a first image, searches for the adventitia in a second image may be limited to a small region about the location of the adventitia in the first image. Thus, the field of search for the adventitia 84 in the second image is reduced by assuming that the adventitia 84 in the second image is in approximately the same position as the adventitia 84 in the first image. Registration may be based on aligning the adventitia 84 in two images, automatically or with human assistance.

Applying 192 inputs to a second image may include using inputs provided either manually or automatically for the analysis of a first image in comparison with or directly for use with a second image. The inputs to the analysis of a first image may also be the result of a calculation by the adapting module 166 as described below for the adapting step 194. Thus, for example, the point 170 selected by a user for a first image may be used in a second image. Likewise, any user-selected, or automatically determined, height 174, 180 or width 176, 182 for a measurement region 172 or sampling region 178 may be used to analyze a new, or compare a second image.

Adapting 194 inputs to a second image may include determining how a second image differs from a first image.

One method for making this determination may be to locate the adventitia 84 and note the location and/or orientation of recognizable irregularities in both the first and second images. By comparing the location, orientation, or both of one or more points on the adventitia, which may be represented by the adventitia datum, the adapting module 166 may calculate how the carotid artery has rotated or translated within the image. One such point may occur where the carotid artery transitions from straight to flared at the dilation point 90. Any translation and/or rotation may then be applied to the point 170 selected by a user to specify the measurement region 172 and the sampling region 178. The rotation and/or translation may also be applied to any automatically determined position of the regions 172, 178.

Figure 10:
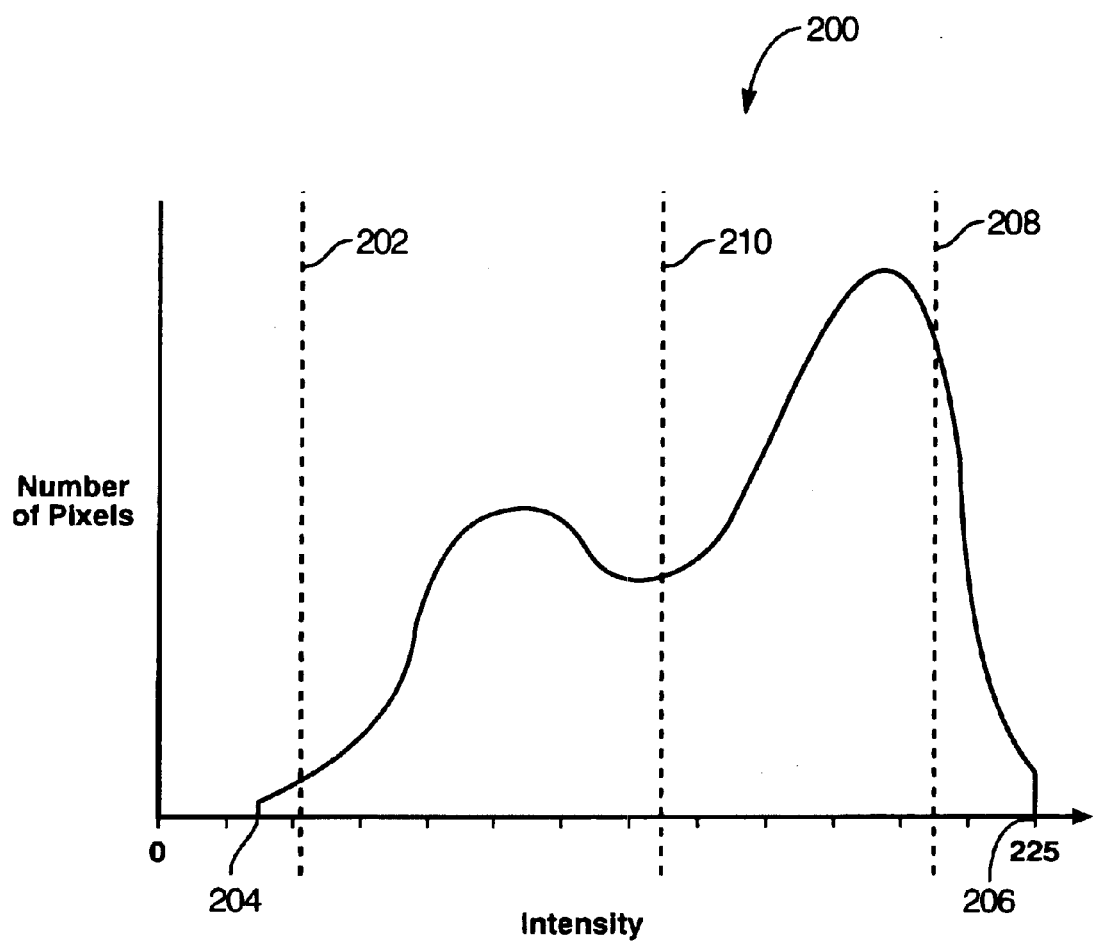
FIG. 10 is a histogram of the intensity of pixels within a sampling region with the location of thresholds marked in accordance with the invention.

Referring to FIG. 10, while referring generally to FIGS. 6–9, the image referencing step 143 may calculate values characterizing a particular image for later use during analysis of the image. For example, the image referencing module 114 may generate a histogram 200 of pixel intensities within the sampling region 178. The image referencing module may also calculate adventitia, media, and lumen thresholds based on the histogram 200 in order to facilitate the location of regions of the image corresponding to the lumen 78, media 82 and adventitia 84.

For example, the lumen threshold 202 may be chosen to be at a suitable (e.g. the 10th) percentile of pixel intensities. Of course other values may be chosen depending on the characteristics of the image. Alternatively, the lumen threshold 202 may be chosen based on the absolute range of pixel intensities present in the sampling region 78. In some embodiments, the lumen threshold 202 may be calculated based on the minimum intensity 204 and maximum intensity 206 apparent in the histogram 200. For example, the lumen threshold 202 may be calculated as a suitable fraction of the maximum difference in pixel intensity. The following formula has been found effective:

lumen threshold=minimum intensity+(fraction)×(maximum intensity−minimum intensity)

A fraction of from 0.05 to 0.25 can work and a value of from about 0.1 to about 0.2 has been successfully used routinely.

The adventitia threshold 208 may be hard coded to be at a fixed (e.g. the 90th) percentile of pixels ranked by intensity. The actual percentile chosen may be any suitable number of values depending on the quality of the image and the actual intensity of pixels in the adventitia portion of the image. Alternatively, the adventitia threshold 208 may equal the maximum intensity 206. This choice is possible inasmuch as the adventitia often appears in ultrasound image as the brightest band of pixels. In some embodiments, the adventitia threshold 208 may also be chosen to be below the highest intensity by a fixed fraction of the maximum difference in intensities. The top 5–25 percent, or other percentage, of the range of pixel intensities may be used, and the top 10 percent has routinely served as a suitable threshold.

A media threshold 210 may be calculated based on the minimum intensity 204 and maximum intensity 206. For example, the media threshold may be calculated according to the formula:

media threshold=minimum intensity+0.25×(minimum intensity+maximum intensity).

This is effectively the 25th percent of the total range of intensities.

Of course, other values for the media threshold 210 are possible depending on the quality of the image and the actual intensity of pixels in the portion of the image corresponding to the media 82. In some embodiments, the media threshold 210 may be equal to the adventitia threshold 208. In some embodiments, the media threshold 210 may be the intensity corresponding to a local minimum on the histogram 200 located between the lumen threshold 202 and the adventitia threshold 208.

The image referencing module 114 may also receive and process inputs to enable a user to manually specify the thresholds 202, 208, 210. For example, the image referencing module 114 may enable a user to manually select a region of pixels in the lumen 78. The average or the maximum intensity of the pixels in this region is then used as the lumen threshold 202. A user may determine adequate values for the adventitia threshold 208 and the media threshold 210 in a like manner relying on maximum, minimum, or average intensity, as appropriate.

In some embodiments, the image referencing module 114 may display the histogram 200 and permit a user to select a threshold based on an informed opinion of what portion of the histogram pixels correspond to the lumen, media, or adventitia. The image referencing module 114 may also simultaneously display the histogram 200 and the ultrasonic image of the carotid artery, highlighting the pixels that fall below, or above, a particular threshold 202, 208, 210. The image referencing module 114 may then permit an operator to vary the lumen threshold 202 and observe how the area of highlighted pixels changes.

Figure 11:
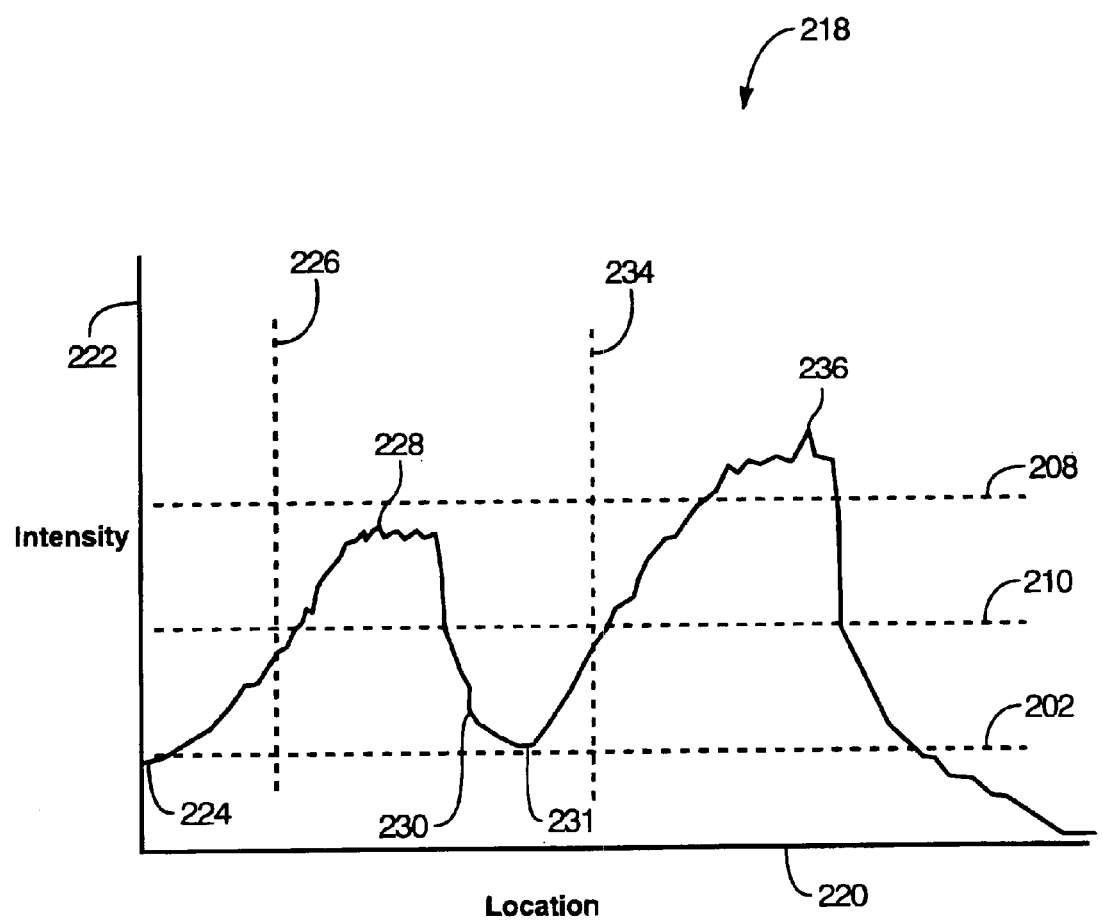
FIG. 11 is a graph of pixel intensities versus their locations for a column of pixels, in accordance with the invention.

Referring to FIG. 11, having determined threshold values 202, 208, 210, the locating module 118 may then analyze lateral columns of pixels to locate the lumen 78, intima 80, media 82, adventitia 84, the lumen/intima boundary, the media adventitia boundary, or any combination, including all. The locating module 118 may analyze lines of pixels oriented horizontally or at another angle, depending on the orientation of the carotid artery within an image. The locating module 118 will typically analyze a line of pixels that extends substantially perpendicular to the boundaries between the layers of tissue.

The graph 218 is an example of a graph of the intensity of pixels versus their location within a column of pixels, with the horizontal axis 220 representing location and the vertical axis 222 representing pixel intensity. Beginning at the left of the graph 218, some significant portions of the graph 218 are: the lumen portion 224, which may be that portion below the lumen threshold 202; the lumen/intima boundary 226, which may correspond to the highest intensity gradient between the lumen portion 224 and the intima maximum 228; the intima maximum 228, a local maximum corresponding to the intima; the media portion 230, which may correspond to the portion of the graph below the media threshold 210; the media dark pixel 231 typically providing a local minimum within the media portion 230; the media/adventitia boundary 234 located at or near the highest intensity gradient between the media dark pixel 231 and the adventitia maximum 236; and the adventitia maximum 236, which is typically the highest intensity pixel in the measurement region 172. It should be understood that the graph 218 is representative of an idealized or typical image, but that noise and poor contrast may cause graphs of pixel columns to appear different.

Figure 12:
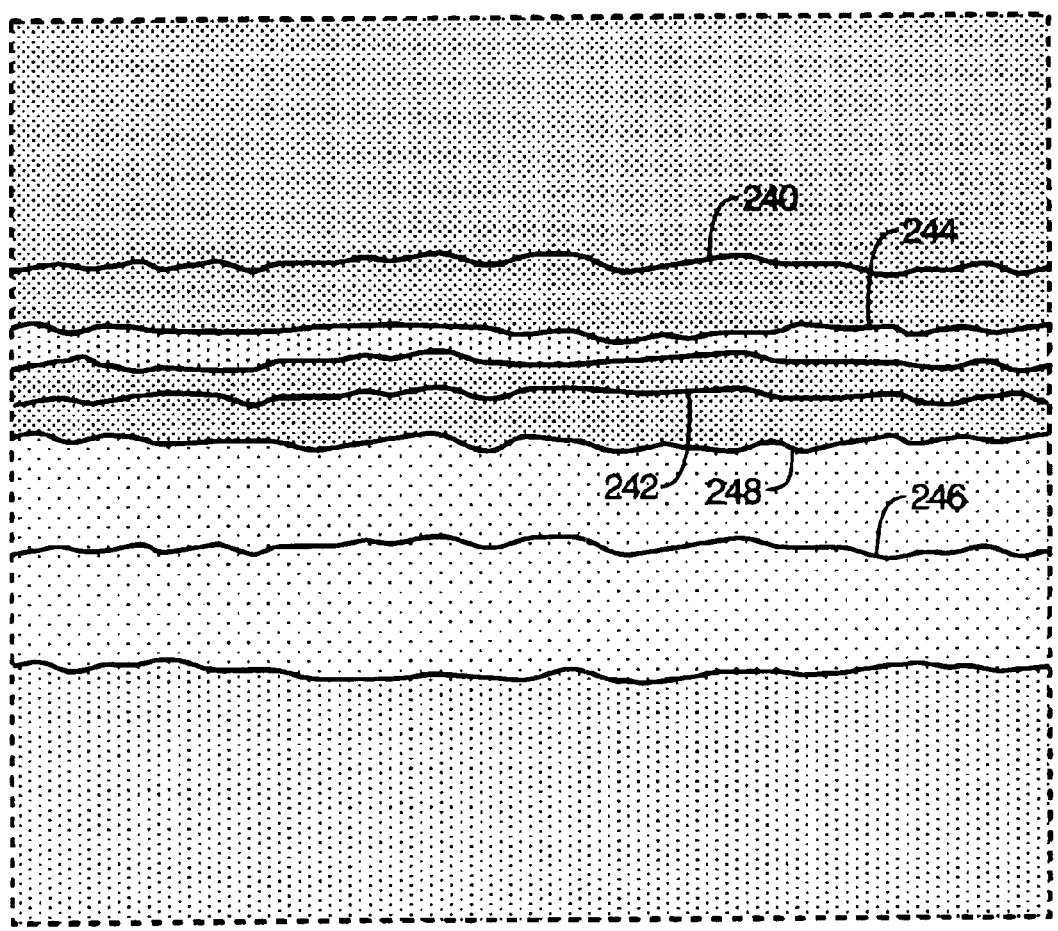
FIG. 12 is a simplified representation of a portion of an ultrasound image of the carotid artery having lumen, media, and adventitia datums superimposed thereon, in accordance with the invention.

Referring to FIG. 12, the locating process 144 may include locating datums to reduce the field of search for the boundaries between layers of tissue. In one embodiment the locating module may identify a lumen datum 240 and media datum 242 that have a high probability of bounding the lumen/intima boundary 244. The media datum 242 and adventitia datum 246 may be chosen such that they have a high probability of bounding the media/adventitia boundary 248. In some embodiments, the locating process 144 may not locate a media datum 242, but rather search between the lumen datum 240 and the adventitia datum 246 for the lumen/intima boundary 244 and the media adventitia boundary 248.

The locating process 144 may allow an operator to manually specify one, or all of, the datums 240, 242, 246, or boundaries 244, 248. Any method for manually specifying a line may be used to specify a boundary 244, 248, or datum 240, 242, 246. For example, an operator may trace a boundary 244, 248 or a datum 240, 242, 246 on a graphical display of an ultrasound image using an input device 22, such as a mouse 36. A user may establish a boundary 244, 248 or datum 240, 242, 246 by clicking at a series of points which are then automatically connected to form a curve. Alternatively, an operator may establish the end points of a line and subsequently establish control points to define the curvature and points of deflection of the line (i.e. a Bezier curve). In still other embodiments, an edge of a measurement region 172 may serve as a lumen datum 240 or adventitia datum 246.

Figure 13:
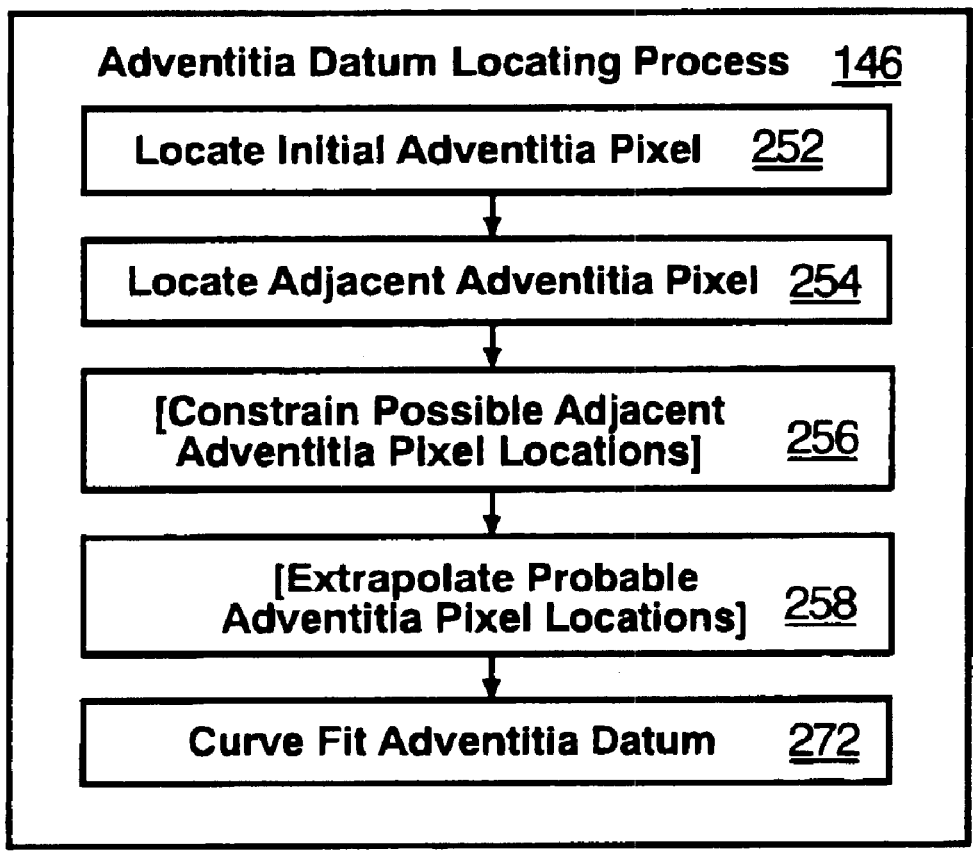
FIG. 13 is a process flow diagram of an adventitia locating process, in accordance with the invention.

Referring to FIG. 13, the adventitia datum locating process 146 may include locating 252 an initial adventitia pixel. The initial adventitia pixel may be found in the column of pixels centered on a user selected point 170. Other suitable approaches may include searching the column of pixels at the extreme left or right of the measurement region or selecting the column at the center of a region selected through an automatic process. The adventitia 84 is typically the brightest portion of the image, so the absolute maximum intensity pixel may be searched for as indicating the location of the adventitia 84. Alternatively, the initial adventitia locating step 252 may comprise prompting a user to manually select an initial adventitia pixel. Yet another alternative approach is to search for a minimum number of contiguous pixels each with an intensity above the adventitia threshold 208 and mark (e.g. label, identify, designate) one of them as the adventitia pixel. This pixel will be used to fit the adventitia datum 246.

The adventitia locating process 146 may also include locating 254 adjacent adventitia pixels. Proceeding column by column, beginning with the columns of pixels next to the initial adventitia pixel, the locating module 118 may search for adjacent adventitia pixels in the remainder of the measurement region 172. The adjacent adventitia pixels may be located in a similar manner to that of the initial adventitia pixel. In certain embodiments, the adventitia pixels may be found in a variety of sequences other than moving from one column to a contiguous column. Sampling, periodic locations, global maximum, left to right, right to left, and the like may all provide starting points, subject to the clarity and accuracy of the image.

Figure 14:
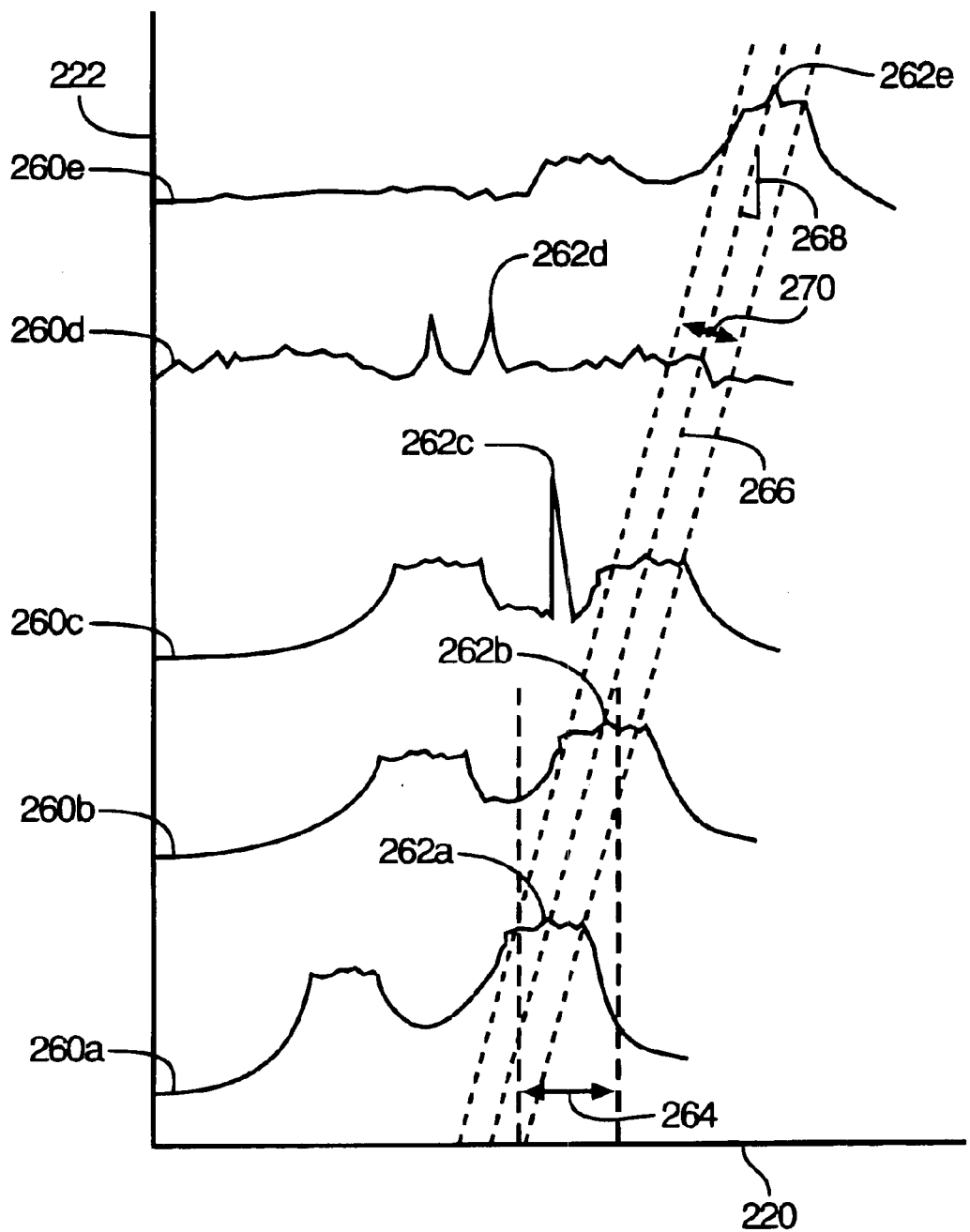
FIG. 14 is a series of graphs representing pixel intensity versus location for columns of pixels with lines representing a process used to compensate for noise and poor contrast, in accordance with the invention.

Referring to FIG. 14, while continuing to refer to FIG. 13, the adventitia locating process 146 may compensate for noise and poor contrast by including a constraining step 256 and an extrapolating step 258. The constraining step 256 may limit the field of search for an adventitia pixel to a small region centered or otherwise registered with respect to the lateral location of the adventitia pixel in an adjacent column.

For example, contiguous columns of pixels may yield a series of graphs 260a–260e. Graph 260a may represent the first column analyzed. Accordingly, the maximum 262a is found and marked as the adventitia pixel, inasmuch as it has the maximum value of intensity. The constraining step 256 may limit searches for a maximum 262b in graph 260b to a region 264 centered on or otherwise registered with respect to the location of the maximum 262a. Maxima falling outside this range may then be dismissed as having a high probability of being the result of noise. That is, a blood vessel is smooth. The adventitia does not wander radically. Rejected maxima may then be excluded from any curve fit of an adventitia datum 246.

The extrapolating step 258 may involve identifying a line 266 having a slope 268 passing through at least two of the maxima 262a–262e. Searches for other maxima may then be limited to a region 270 limited with respect to the line 266. Thus, in the illustrated graphs, the maxima 262c in graph 260c is not within the region 270 and may therefore be ignored. In some instances, the extrapolating step may involve ignoring multiple graphs 260a–260e whose maxima 262a–262e do not fall within a region 264, 270.

As illustrated, a graph 260d may have a maximum 262d outside the region 270 as well, whereas the graph 260e has a maxima 262e within the region 270. The number of columns that can be ignored in this manner may be adjustable by a user or automatically calculated based on the quality of the image. Where the image is of poor quality the extrapolating step 258 may be made more aggressive, looking farther ahead for an adequate (suitable, clear) column of pixels. In some embodiments, the maxima 262a–262e used to establish the line 266 may be limited to those that are in columns having good high contrast.

Referring again to FIG. 13, a curve fitting step 272 may establish an adventitia datum 246, a curve fit to the adventitia pixels located in the columns of pixels. A curve fit is typically performed to smooth the adventitia 84 and compensate for noise that does not truly represent the adventitia 84. In one embodiment, the curve fitting step 272 may involve breaking the measurement region into smaller segments (pieces) and curve fitting each one, piecewise. A function, such as a second order polynomial, a sinusoid or other trigonometric function, an exponential function or the like may be selected to be fit to each segment. The segments may be sized such that the path of adventitia pixels is likely to be continuous, be monotonic, have a single degree of curvature (e.g. no 'S' shapes within a segment) or have continuity of a derivative. A segment width of 0.5 to 2 mm has been found to provide a fair balance of adequate accuracy, function continuity, and speed of calculation Other embodiments are also possible. For example, wider segments may be used with a third order polynomial interpolation to accommodate a greater likelihood of inflection points (an 'S' shape) or derivative continuity in the adventitia pixel path. However, a third order polynomial interpolation imposes greater computational complexity and time. Another alternative is to use very narrow segments with a linear interpolation. This provides simple calculations, functional continuity, but no first derivative continuity.

In some embodiments, the segments curve fitted may overlap one another. This may provide the advantage of each curve fitted segment having a substantially matching slope with abutting segments at the point of abutment. However, this approach may introduce computational complexity by requiring the analysis of many pixels twice. However, it provides for comparatively simpler computations for each segment.

Figure 15:
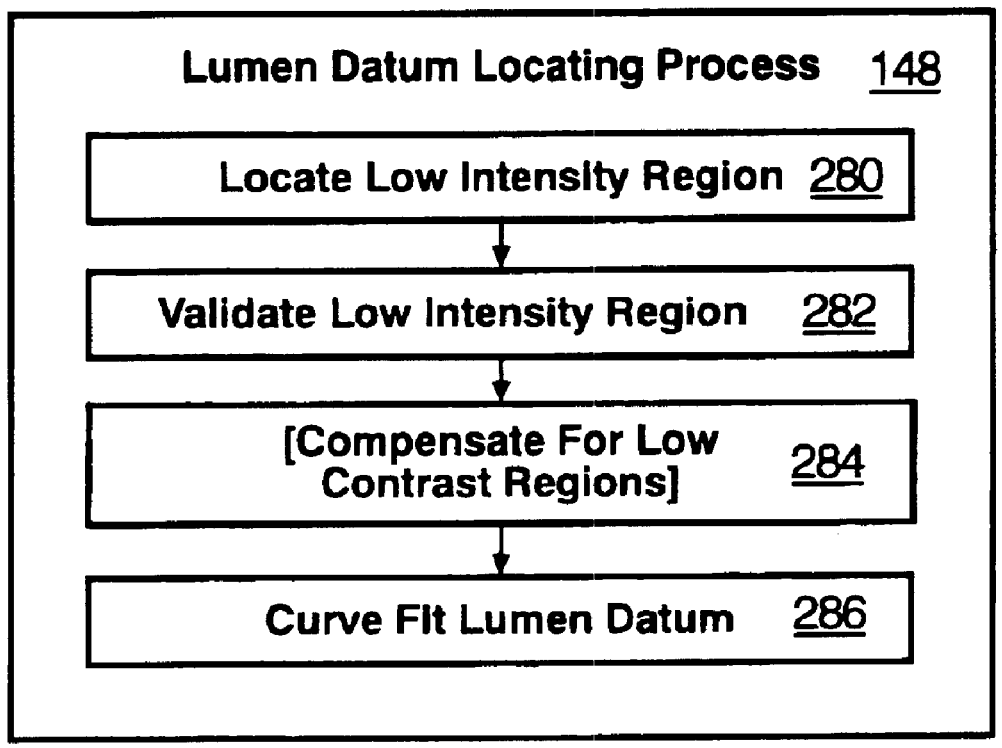
FIG. 15 is a process flow diagram of a lumen locating process, in accordance with the invention.

Referring to FIG. 15, The lumen datum locating process 148 may identify the portion of an image corresponding to the lumen 78 and establish a lumen datum 240. The lumen datum locating process 148 may include locating 280 a low intensity region. This step may include finding, in a column of pixels, a specific number of contiguous pixels below the lumen threshold 202. The search for a band of low intensity pixels typically begins at the adventitia 84 and proceeds toward the center of the lumen 78. A region four pixels wide has been found to be adequate. Alternatively, step 280 may include searching for a contiguous group of pixels whose average intensity is below the lumen threshold 202.

Having located a low intensity region, the next step may be a validating step 282. In some instances, dark areas within the intima/media region may be large enough to have four pixels below the lumen threshold 202. Accordingly, a low intensity region may be validated to ensure that it is indeed within the lumen 78. One method of validation is to ensure that the low intensity region is adjacent a large intensity gradient, which is typically the lumen/intima boundary 226. The proximity to the intensity gradient required to validate a low intensity region may vary.

For example, validation may optionally require that the low intensity region be immediately next to the large intensity gradient. Alternatively, validation may only require that the low intensity region be within a specified number of pixels (e.g. distance) from the high intensity gradient. Where a low intensity region has a high probability of being invalid, the lumen datum locating process 148 may be repeated, beginning at the location of the invalid low intensity region found during the first iteration and moving away from the adventitia 84.

The lumen datum locating process 148 may also include a compensating step 284. In some cases, it may be difficult to verify that a low intensity region is proximate the lumen/intima boundary 244, because limitations in the ultrasound imaging process may fail to capture intensity gradients, but rather leave regions of the image with poor contrast. Accordingly, a compensating step 284 may include methods to compensate for this lack of contrast by extrapolating, interpolating, or both, the boundaries into areas of poor contrast. Validating 282 may therefore include verifying a low intensity region's proximity to an interpolated or extrapolated boundary.

A curve fitting step 286 may incorporate the found low intensity regions into the lumen datum 240. In some embodiments, a path comprising the first pixel found in the low intensity region of each column is curve fitted to establish the lumen datum 240. In embodiments that use an average value of intensity to locate the lumen, a centrally (dimensionally) located pixel in a group of pixels averaged may be used to curve fit the lumen datum 240. The curve fitting step 286 may curve fit the pixel path in the manner discussed above in conjunction with the adventitia datum locating process 146.

Figure 16:
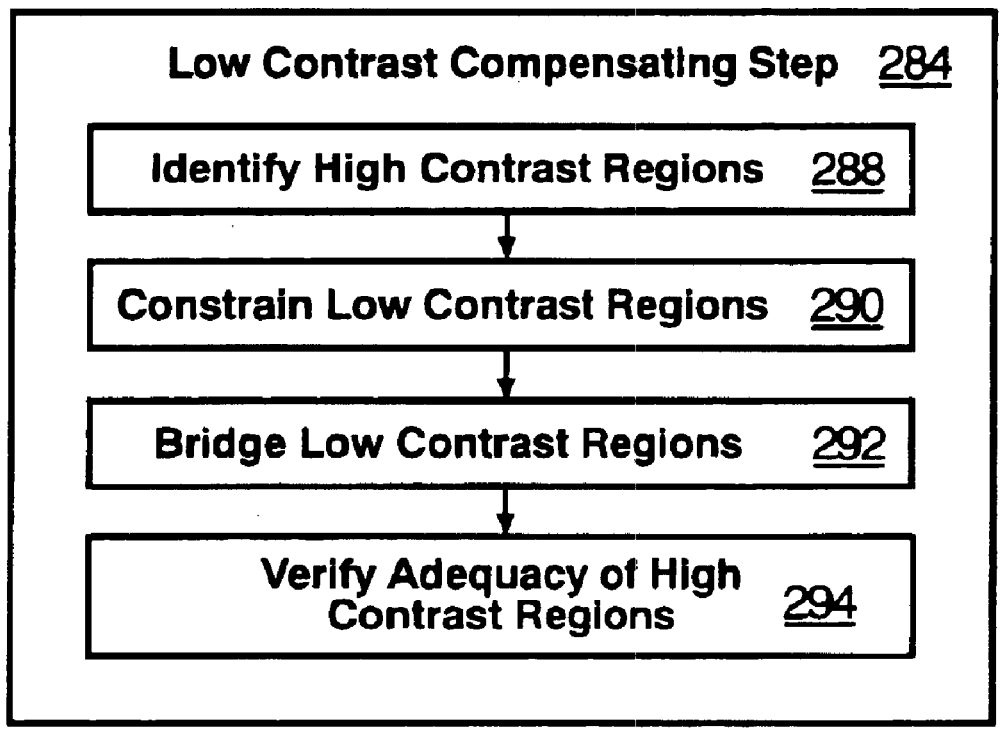
FIG. 16 is a process flow diagram of a process for compensating for low contrast, in accordance with the invention.

FIG. 16 illustrates one method for implementing an optional low contrast compensating step 284, which includes an identifying step 288, a constraining step 290, a bridging step 292, and a verifying step 294. An identifying step 288 may identify portions of the measurement region 172 that appear to be of high quality. Identifying 288 may include identifying a horizontal region at least three to five pixel columns wide, with each column having comparatively high contrast. A larger or smaller horizontal region may be chosen based on the nature and quality of the image. In some embodiments, the degree of contrast may be determined by looking for the largest, or sufficiently large, intensity gradient in a column. The value of the gradient sufficient to qualify a column of pixels as "high contrast" may be hard coded, user selected, automatically selected, a combination thereof, or all of the above, based on the characteristics of the image. In some embodiments, the intensity gradient required may be a certain percentage of the maximum intensity gradient found in the sampling region 178.

Identifying 288 may also include verifying that the large intensity gradients in each column of a horizontal region occur at approximately the same position within the column, deviating from one another by no more than a predetermined number of pixels. Thus, for example, if in one column of pixels a high intensity gradient is located at the 75th pixel, identifying 288 may include verifying that a high intensity gradient in the adjacent column occurs somewhere between the 70th and 80th pixel. Columns whose high intensity gradient is not located within this region may be excluded from the horizontal region of high intensity pixels for purposes of evaluating the quality of the image and extrapolating and interpolating gradient or boundary locations. In some embodiments, only regions of a specific width having contiguous columns with high intensity gradients occurring at approximately the same lateral position are treated as high contrast regions.

A constraining step 290 may attempt to identify the location of the lumen/intima boundary 226, or, more generally, any boundary or feature, in the absence of high contrast. One manner of accomplishing this is to constrain the area of search. Constraining 290 may therefore search for a the largest gradient in a low contrast region between two high contrast regions by restricting its search to a region centered on a line drawn from the large intensity gradient in one of the high contrast regions to the large intensity gradient in the second.

Constraining 290 may also include using a different value to define the boundary. Whereas, in a high contract region a comparatively large value may be used to identify, limit, or specify which gradients represent boundaries. Constraining 290 may include determining the maximum intensity gradient in a comparatively lower contrast region and using some percentage of this smaller value to define which gradients are sufficiently large to represent a boundary. Likewise, constraining 290 may comprise looking for the steepest gradient above some minimum value within a constrained region.

A bridging step 292 may include interpolating the location of a boundary or other intensity gradient in a low contrast region based on the location of the boundary or gradient in comparatively higher contrast regions on either side. Optionally, in some embodiments, the location of a boundary or gradient may be extrapolated based on the location of a high contrast region to one side of a low contrast region.

A verifying step 294 may verify that the high contrast regions are adequate to justify interpolation and extrapolation into the comparatively lower contrast regions. A verifying step 294 may include comparing the number of columns in these "high" contrast regions to the number of columns in the "low" contrast regions. Where more pixel columns are in low contrast regions than are in high contrast regions, extrapolation and interpolation may not improve accuracy.

Figure 17:
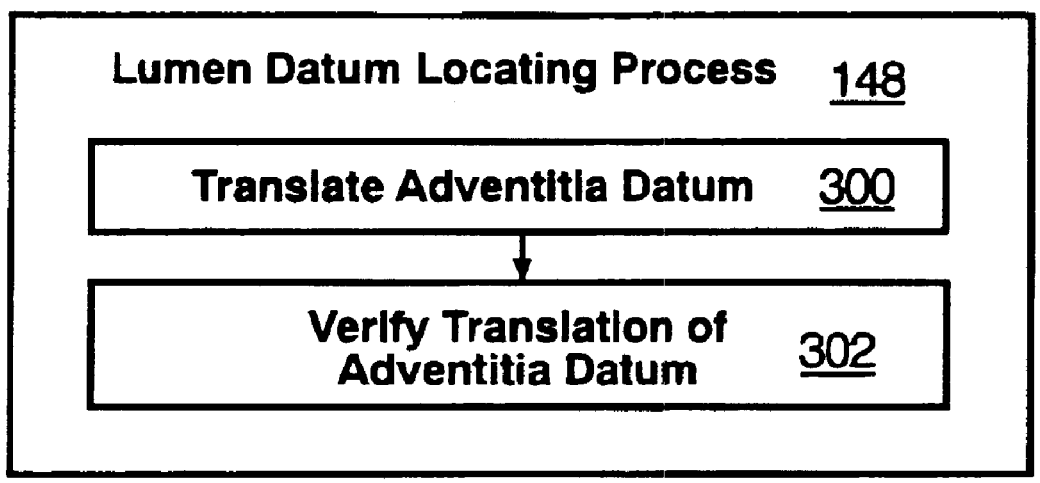
FIG. 17 is a process flow diagram of an alternative lumen locating process, in accordance with the invention.
Figure 18:
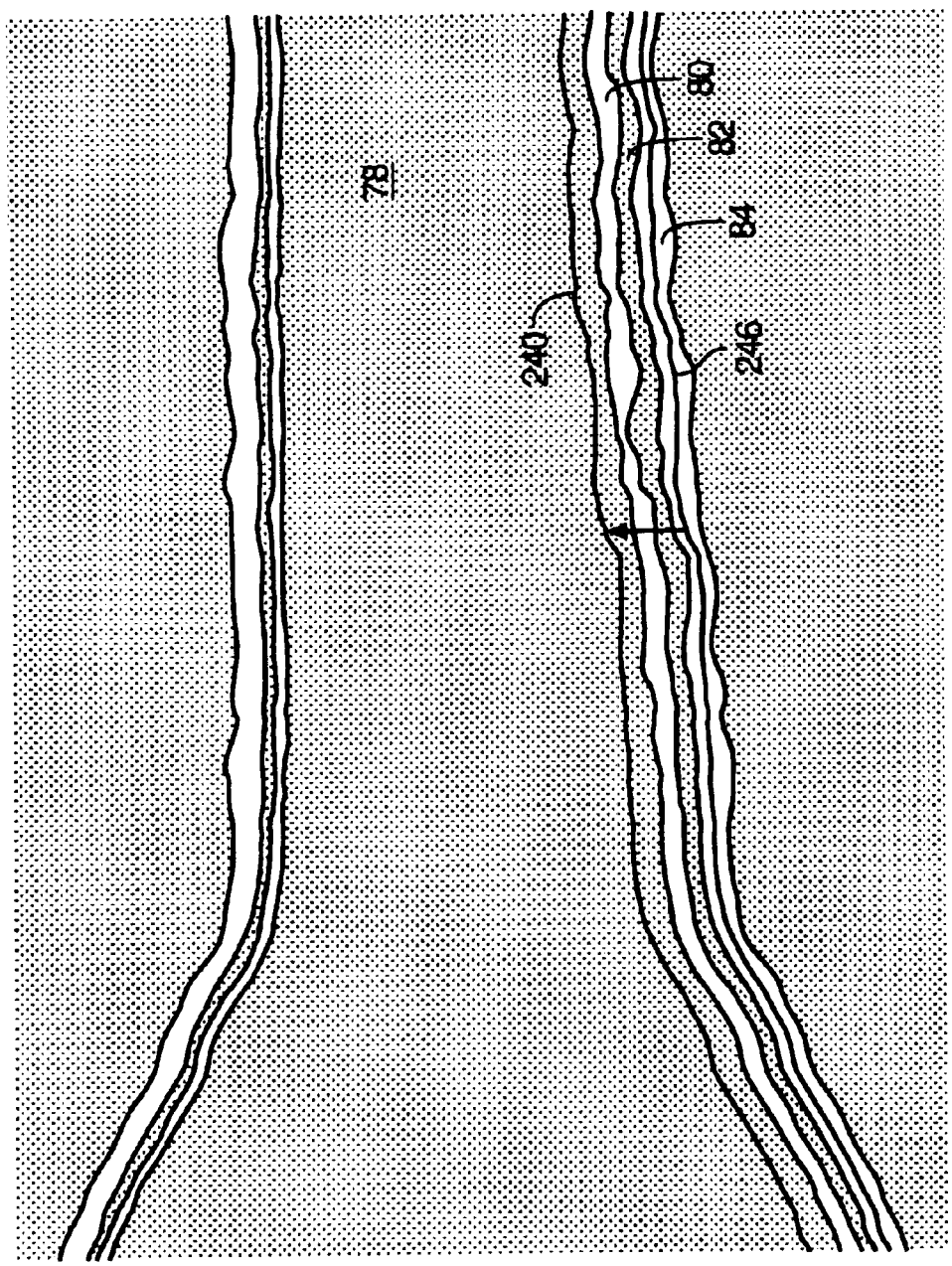
FIG. 18 is a simplified representation of an ultrasonic image of the common carotid artery with lines representing the process of adapting an adventitia datum to find a lumen datum, in accordance with the invention.

Referring to FIG. 17, in an alternative embodiment, the lumen datum locating process 148 includes a translating step 300 and a translation verifying step 302. Referring to FIG. 18, the translating step 300 may include translating the adventitia datum 246 toward the center of the lumen 78. The translation verifying step 302 may average the intensities of all the pixels lying on the translated path. Where the average value, mean value, or some number of total pixels correspond to an intensity that is less than the lumen threshold 202, or some other minimum value, the translation verifying step 302 may include establishing the translated adventitia datum 246 as the lumen datum 240. Alternatively, the translation verifying step 302 may include marking the translated adventitia datum 246 as the lumen datum 240 only where the intensity of all pixels lying on the translated datum 246 are below the lumen threshold 202, or some other minimum value. Alternatively, the translated adventitia datum 246 may simply serve as a starting point for another curve fit process, or serve as the center, edge, or other registering point, for a region constraining a search for a lumen datum 240, for example the method of FIG. 15 could be used to search for a lumen datum 240 within a constrained search region.

Figure 19:
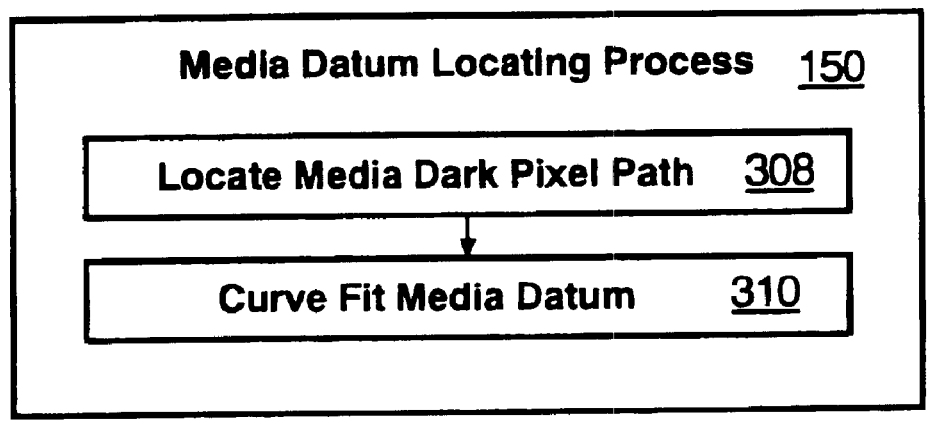
FIG. 19 is a process flow diagram of a media datum locating process, in accordance with the invention.

Referring to FIG. 19, the media datum locating process 150 may include a locating step 308 and a curve fitting step 310. A locating step 308 may identify a media dark pixel path that is subsequently adapted to yield a media datum 242. The curve fitting step 310 may curve fit a media dark pixel path to yield a media datum 242 in a like manner as other curve fitting steps already discussed in accordance with the invention. In some embodiments, the media datum locating process 150 may be eliminated and the lumen datum 240 may be used everywhere the media datum 242 is used to limit fields of search. In still other embodiments, a lumen datum 240 may be eliminated and the adventitia 84 alone may constrain searches for the boundaries between layers of tissue. For example, searches for the media/adventitia boundary may simply begin at the adventitia datum 246 and move toward the lumen 78.

Figure 20:
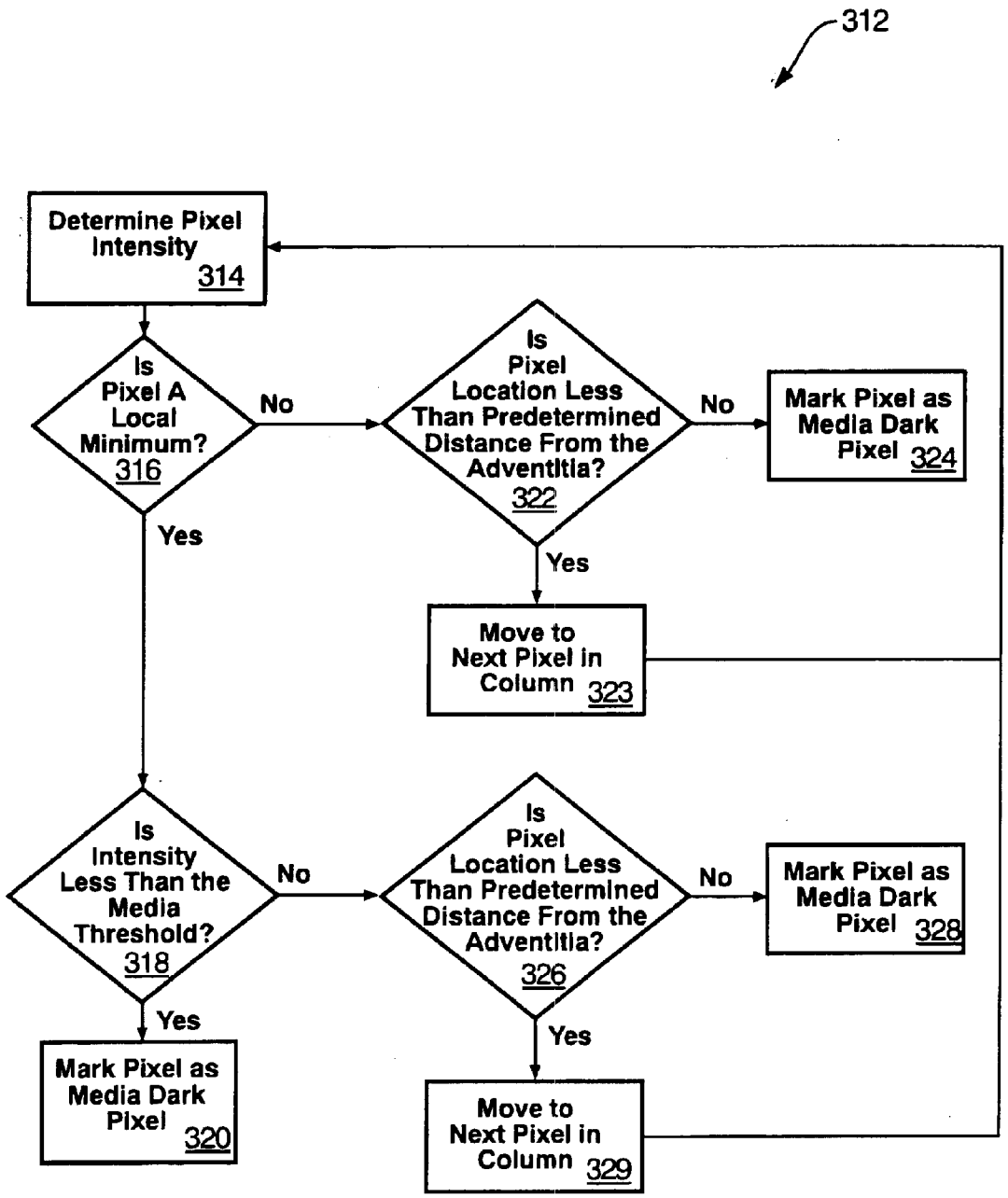
FIG. 20 is a flow chart representing a process for locating a media dark pixel in a column of pixels, in accordance with the invention.

Referring to FIG. 20, the locating process 312 illustrates one method for locating 308 the media dark pixel path. The process 312 may be carried out on the columns of pixels in the measurement region 172. The process 312 may begin by examining a pixel lying on, or near, the adventitia datum 246. After determining 314 the intensity of a pixel, the process 312 may determine 316 whether the pixel is a local minimum. If so, the process 312 may determine 318 if the pixel intensity is less than the media threshold 210. If so, the pixel is marked 320 or designated 320 as a media dark pixel, and the process 312 is carried out on another column of pixels.

If a pixel is not a local minimum, the process 312 may determine 322 whether the pixel is located less than a predetermined distance from the adventitia 84. An adequate value for this distance may be about one half to two thirds of the distance from the adventitia 84 to the lumen 78. The adventitia datum 246 and the lumen datum 240 may be used to specify the location of the adventitia 84 and the lumen 78 for determining the distance therebetween. If the pixel is less than the specified distance from the adventitia 84, then the process 312 moves 323 to the next pixel in the column, in some embodiments moving away from the adventitia 84, and the process 312 is repeated. If the pixel is spaced apart from the lumen 78 by the specified distance, then it is marked 324 as a media dark pixel and the process 312 is carried out for any remaining columns of pixels.

If a minimum value of intensity is not less than the media threshold 210, the process 312 may determine 326 whether the distance from the pixel to the adventitia 84 is greater than or equal to the same predetermined value as in step 322. If greater than or equal to that value, the corresponding pixel is marked 328 as a media dark pixel and the process 312 is carried out on any remaining columns. If less, then the process 312 moves 329 to the next pixel in the column, typically moving toward the adventitia 84, and the process 312 is repeated.

Figure 21:
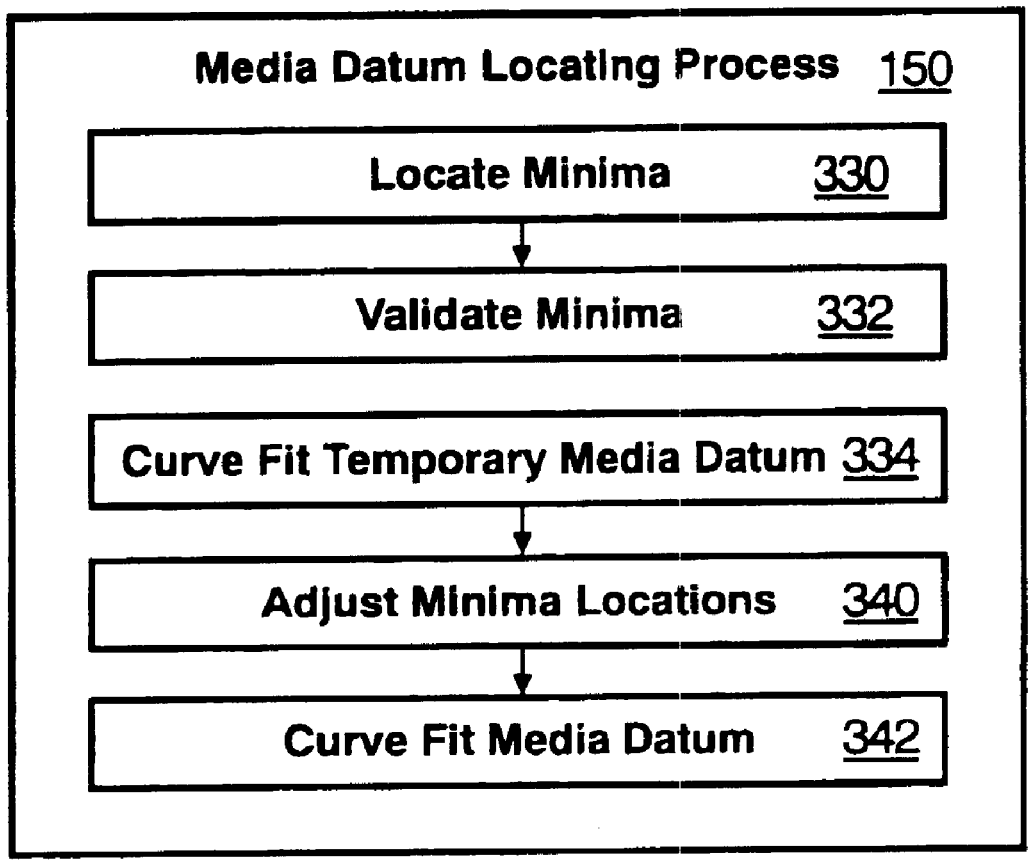
FIG. 21 is a process flow diagram representing an alternative media datum locating process, in accordance with the invention.

FIG. 21 illustrates another embodiment of a media datum locating process 150. A minimum locating step 330 may look for local minima of intensity in each column of pixels, between the adventitia 84 and the lumen 78. In some embodiments, the minimum locating step 330 may search for a local minimum between the adventitia datum 246 and the lumen datum 240. The minimum locating step 330 may search for minima beginning at the adventitia datum 246 and moving toward the lumen datum 240. In columns of pixels having poor contrast, the minimum locating step 330 may include extrapolating or interpolating the probable location of a local minimum representing the media based on the location of validated minima on either side, or to one side, of a column of pixels, or columns of pixels, having poor contrast. The probable location of a local minimum determined by extrapolation or interpolation may then be used as the location of the media dark pixel in a column, rather than an actual, valid local minimum.

Once a minimum is found, a validating step 332 may verify that the minimum is likely located within the media 82. A minimum may be validated 332 by ensuring that it is below the media threshold 210. A minimum may also be validated 332 by ensuring that it is adjacent a high intensity gradient located between the minimum and the adventitia datum 246, inasmuch as the comparatively dark media 82 is adjacent the comparatively brighter adventitia 84, and these will therefore have an intensity gradient between them. The validating step 332 may include marking valid minima as media dark pixels used to establish a media datum 242. If an inadequate minimum is found, the process 150 may be repeated beginning at the location of the inadequate minimum and moving toward the lumen 78.

A validating step 332 may also include inspecting the location of the minima. Validation 332 may ensure that only those minima that are within a specified distance from the adventitia 84 are marked as media dark pixels used to calculate the media datum 242. A workable value for the specified distance may be from about one-half to about two-thirds of the distance from the adventitia 84 to the lumen 78. In the event that no minimum falls below the media threshold 210, is located proximate a large intensity gradient, or both, validation 332 may include marking a pixel a specified distance from the adventitia as the media dark pixel used to calculate (curve fit) the media datum 242.

Figure 22:
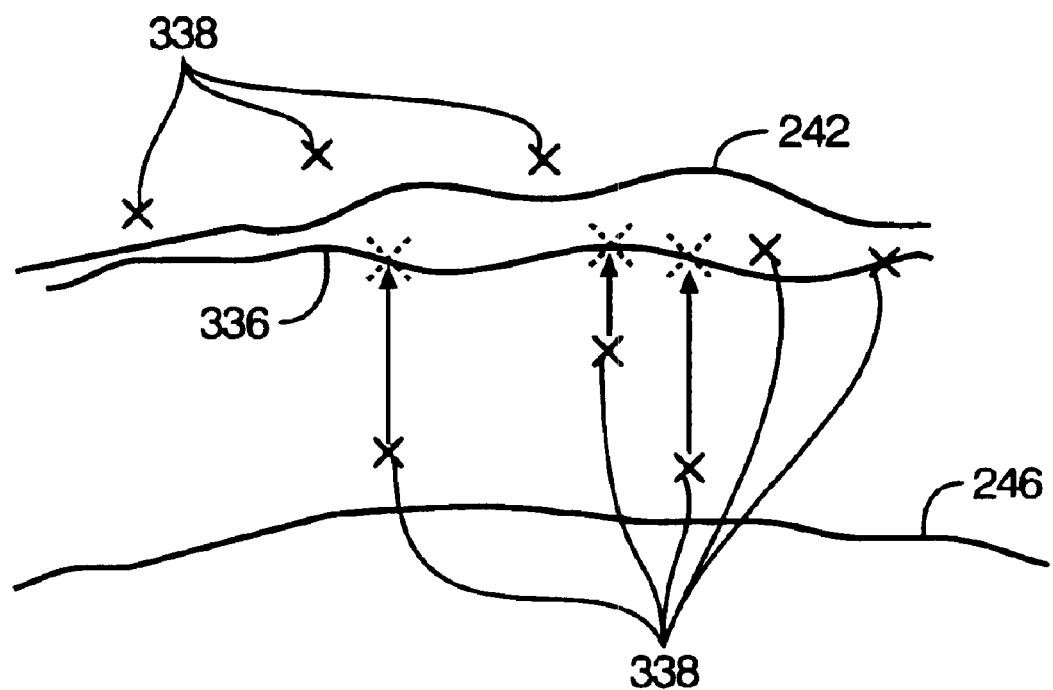
FIG. 22 is a graphical representation of the process of adjusting minima locations in order to find a media datum.

Referring to FIG. 22, while still referring to FIG. 21, a curve fitting step 334 may establish a temporary media datum 336 comprising a curve fit of the media dark pixels 338 located laterally in each column of pixels over the domain of the image. The curve fitting step 334 may use any of the curve fitting methods discussed above in conjunction with other datums or other suitable methods.

An adjustment step 340 may alter the locations of the media dark pixels 338 used to calculate the media datum 242. For example, each media dark pixel 338 may be examined to see whether it is located between the temporary media datum 338 and the adventitia datum 246. The media 82 makes no actual incursions into the adventitia 84. Those media dark pixels between the adventitia datum 246 and the temporary media datum 338 may be moved to, or replaced by points or pixels at, the temporary media datum 336. A curve fitting step 342 may then curve fit the media datum 242 to the modified set of media dark pixels 338. The curve fitting step 342 may make use of any of the curve fitting methods discussed in conjunction with other datums or other suitable methods. Alternatively, the temporary media datum 338 itself may serve as the media datum 242.

Figure 23:
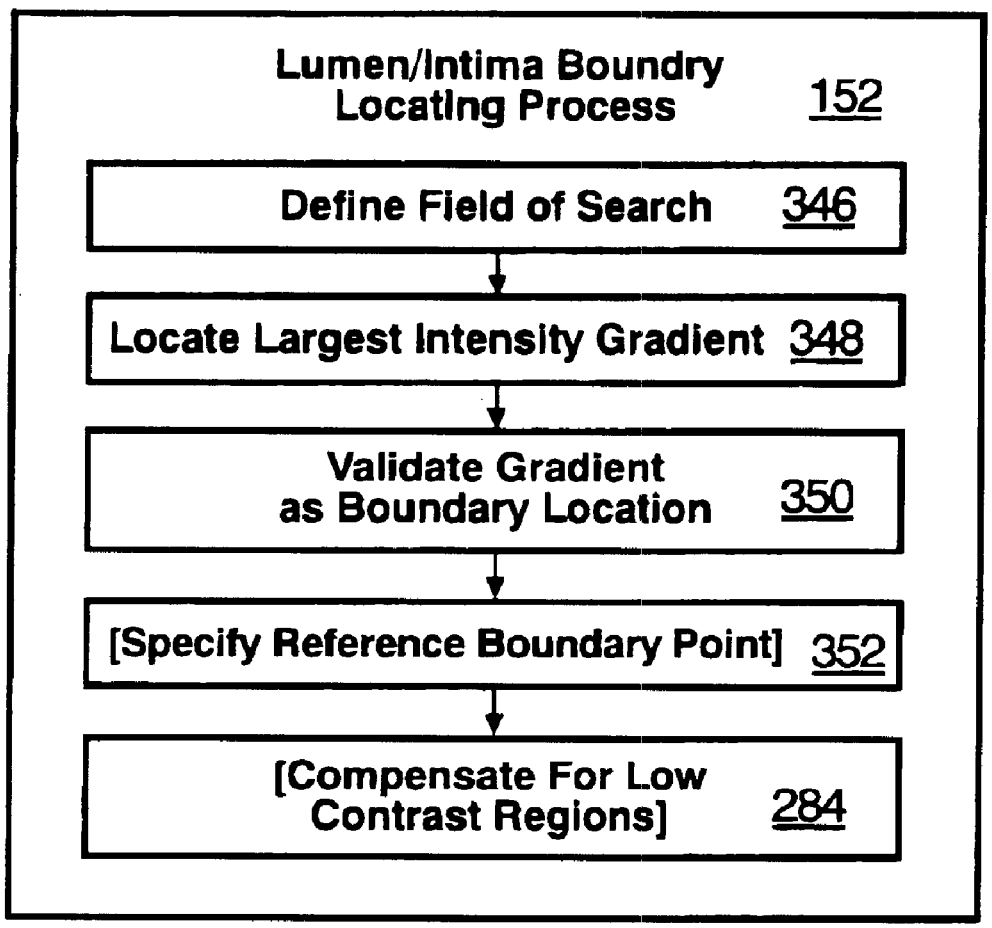
FIG. 23 is a process flow diagram of a lumen/intima boundary locating process, in accordance with the invention.

FIG. 23 illustrates the lumen/intima boundary locating process 152. A defining step 346 may define 346 the field searched. For example, in one embodiment, the field of search is limited to the area between the lumen datum 240 and the media datum 242. Defining 346 the field of search may include searching only the region between the lumen datum 240 and a first local maximum found when searching from the lumen datum 240 toward the media datum 242. Some embodiments may require that the local maximum have an intensity above the media threshold 210. In some embodiments, defining 346 the field of search may include manually or automatically adjusting the location of the lumen datum 240 and/or the media datum 242. For example, a user may click on a graphical representation of the lumen datum 240 and translate it laterally to a different position to observe the quality of fit or correspondence. In still other embodiments, the field of search may be defined 346 as the region between the adventitia datum 246 and an edge of the measurement region 172 lying within the lumen.

In some embodiments, an operator may select a point or points approximately on the lumen/intima boundary 244. Defining 346 the field of search may include searching only a small region centered on the operator selected points, or a line interpolated between the operator selected points. Alternatively, an operator or software may select or specify a point, or series of points, just within the lumen 78 to define one boundary of the search region.

A locating step 348 may begin at the lumen datum 240, or other limiting boundary, such as the edge of a measurement region 172, and search toward the media datum 242 for the largest positive intensity gradient. In embodiments where a media datum 242 is not located, the locating step 348 may search from the lumen datum 240, or other boundary, toward the adventitia datum 246 for the largest positive intensity gradient. A validating step 350 may verify that a gradient likely represents the lumen/intima boundary 244. In some embodiments, the locating step 348 may involve searching for the largest negative intensity gradient when moving from the adventitia datum 246, or local maximum above the media threshold 210, toward the lumen datum 240, or media datum 242. In some embodiments, validating 350 may include rejecting gradients where the pixels defining the gradient are below a specific threshold value, such as the lumen threshold 202.

The defining step 346, locating step 348, and the validating step 350 may be repeated until the largest (steepest), valid intensity gradient is found. Accordingly defining 346 the field of search may include limiting the field of search to those columns of pixels that have not hitherto been examined. For example, defining 346 the field of search may include limiting the regions searched to the region between an invalid gradient and the media datum 242 or a first local maximum above the media threshold 210.

An optional specifying step 352 may enable an operator to manually specify the location of the lumen/intima boundary 244 at one or more points. An optional compensating step 284, as discussed above, may extrapolate or interpolate the location of the lumen/intima boundary 244 in comparatively low contrast regions based on portions of the lumen/intima boundary 244 found in a comparatively high contrast region. A compensating step 284 may also extrapolate or interpolate between operator specified points and high contrast regions.

Figure 24:
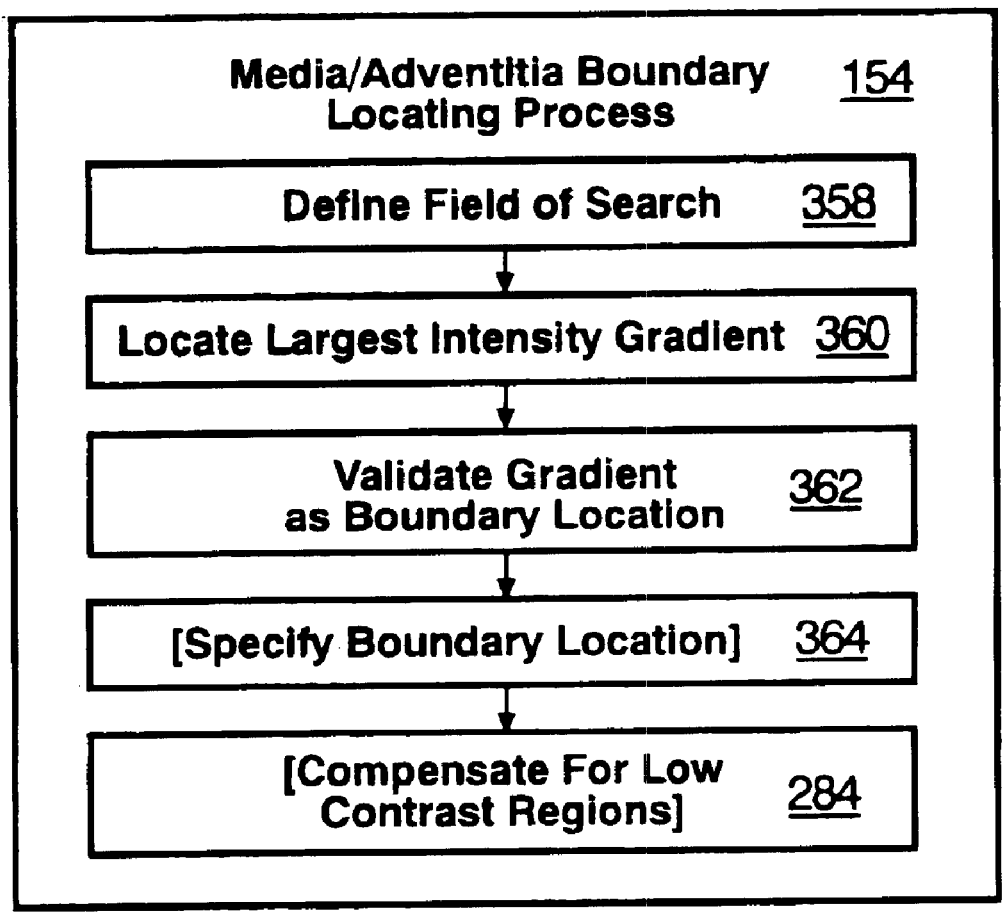
FIG. 24 is a process flow diagram of a media/adventitia boundary locating process, in accordance with the invention.

FIG. 24 illustrates one embodiment of a media/adventitia boundary locating process 154. A defining step 358 may define the field searched. For example, in one embodiment, the field of search is limited to the portion of a column of pixels between the media datum 242 and the adventitia datum 246. Alternatively, the field of search may be limited to the region between the lumen datum 240 and the adventitia datum 246. In still other embodiments, the field of search may be defined 358 as the region between the adventitia datum 246 and an edge of the measurement region 172 lying within the lumen. In some embodiments, defining 358 the field of search may also include manually or automatically translating the media datum 242, the adventitia datum 246, or both. In still other embodiments, the field of search may be limited to the area between the media datum 242 and a local maximum having a corresponding intensity above the adventitia threshold 208 or other minimum value.

A locating step 360 may identify the largest positive gradients within the field of search. The locating step 360 may involve examining each pixel starting at the media datum 242, or other boundary, such as an edge of a measurement region 172 or the lumen datum 240, and moving toward the adventitia datum 246. The validating step 362 may verify that an intensity gradient has a high probability of being the media/adventitia boundary 248. Validating 362 may include rejecting gradients where the pixels defining the gradient are below a certain value, such as the media threshold 210.

Where a gradient is rejected during the validating step 362, the defining step 358, locating step 360, and validating step 362 may be repeated to find and validate the next largest intensity gradient until the largest valid intensity gradient is found. The defining step 358 may therefore also include limiting the field of search to the region between the media datum 242, or other boundary, and the location of an invalid intensity gradient.

Optionally, a specifying step 364 may enable an operator to manually specify the approximate location of the media/adventitia boundary 248 at one or more points. A compensating step 284, as discussed above, may extrapolate or interpolate the location of the media/adventitia boundary 248 in low contrast regions based on portions of the media/adventitia boundary 248 found in high contrast regions and/or operator specified points along the media/adventitia boundary 248.

Figure 25:
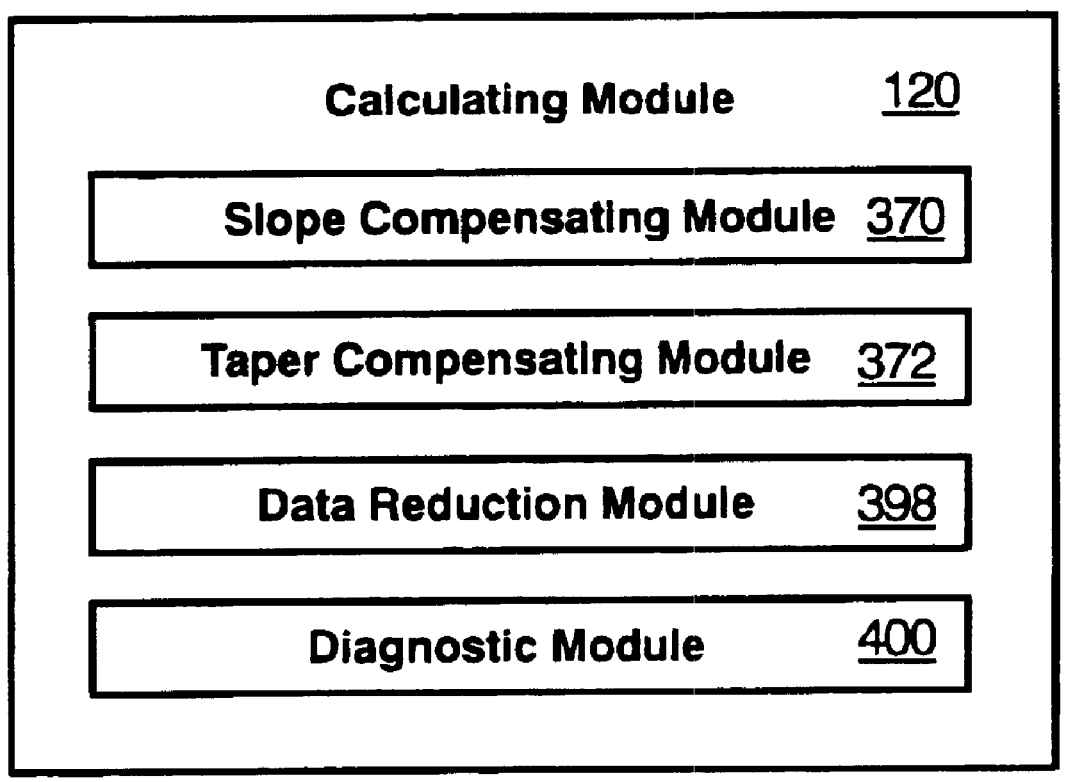
FIG. 25 is a schematic block diagram of data structures suitable for implementing a calculating module in accordance with the invention.

Referring to FIG. 25, a calculating module 120 may calculate an IMT value based on the distance between the lumen/intima boundary 244 and the media/adventitia boundary 248. In some embodiments, the calculating module 120 may calculate the distance between the lumen/intima boundary 244 and the media/adventitia boundary 248 for each column of pixels and average them together to yield a final value. The calculating module 120 may also convert a calculated IMT value to its actual, real world, value based on calibration factors calculated by the calibration module 112.

In some embodiments, the calculating module 120 may remove (filter) spikes or other discontinuities of slope on the media/adventitia boundary 248. For example, the calculating module 120 may look for spikes whose height is a specific multiple of their width. For instance, spikes having a height three (or other effective multiple) times the width of their base may be identified. The portion of the media/adventitia boundary 248 forming the spike may be replaced with an average of the location of the boundary on either side of the spike. The calculating module 120 may likewise remove spikes from the lumen/intima boundary 244.

The calculating module 120 may also curve fit either the media/adventitia boundary 248, the lumen/intima boundary 244, or both. In some embodiments, the calculating module 120 will curve fit the boundaries 244,248 after having removed spikes from the boundaries 244, 248, in order that clearly erroneous data not influence the resulting curve fit.

The calculating module 120 may include a slope compensating module 370. The slope compensating module 370 may adjust IMT measurements for the angle 100 of the carotid artery relative to the horizontal direction 74. For example, in some embodiments, the slope compensating module 370 may multiply an IMT measurement by the cosine of the angle 100. The angle 100 may be calculated by fitting a line to the lumen/intima boundary 244, the media/adventitia boundary 248, or a line of pixels at the midpoint between the lumen/intima boundary 244 and the media/adventitia boundary 248, for each column of pixels. The angle 100 may be set equal to the angle of the line relative to the horizontal direction 74. Alternatively, the angle 100 may be calculated using a line fit to one, or a combination, of the lumen datum 240, the media datum 242, and/or the adventitia datum 246. In some embodiments, the angle 100 may be calculated based on a line connecting the leftmost and rightmost points comprising the lumen datum 240, media datum 242, adventitia datum 246, lumen/intima boundary 244, or media adventitia boundary 248. Alternatively, an operator may select two points which the slope compensating module 370 may then use to define the angle 100.

The calculating module 120 may also include a taper compensating module 372 for adjusting an IMT measurement to counter the effect that any taper of the IMT thickness may have on a measurement. One method for eliminating this type of variation is to measure the IMT in a region where tapering effects are not present. For example, the IMT of the segment 98 located between 10 mm and 20 mm away from the flared portion 90 typically does not taper greatly.

The taper compensating module 372 may locate the bifurcation by searching for the dilation point 90. In one embodiment, the taper compensating module 372 fits a straight line to the substantially straight portion of the adventitia 84. The taper compensating module 386 may then extrapolate this line toward the bifurcation, examining the intensity of the pixels lying on the line. Where the pixels falling on the line consistently have an intensity below the lumen threshold 202, the line is extending into the lumen 78. The location where the line initially encounters the low intensity pixels will correspond approximately to the dilation point 90 and the approximate location of the bifurcation. Of course, a variety of methods may be used to locate the dilation point 90.

Figure 26:
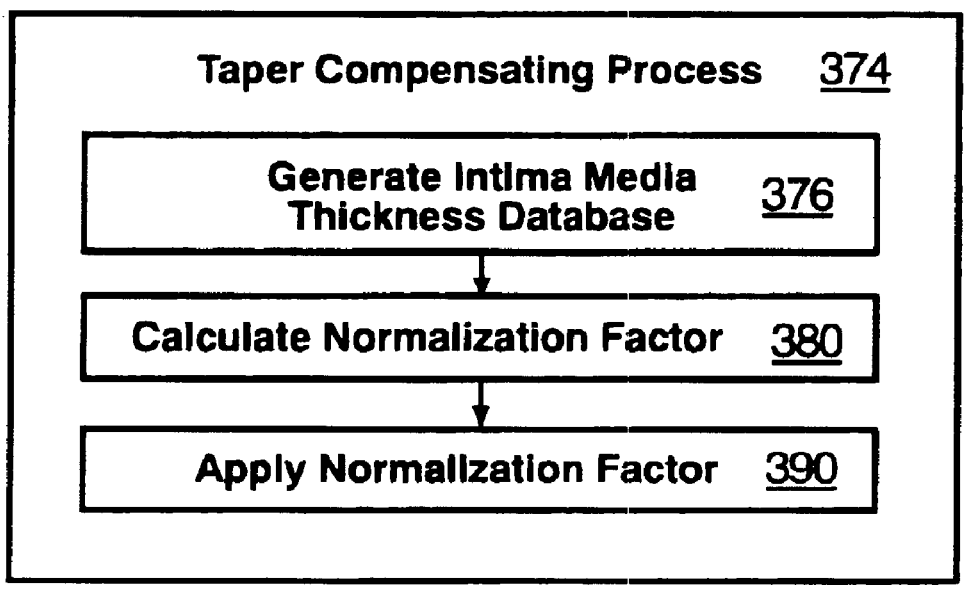
FIG. 26 is a process flow diagram of a taper compensating process in accordance with the invention.
Figure 27:
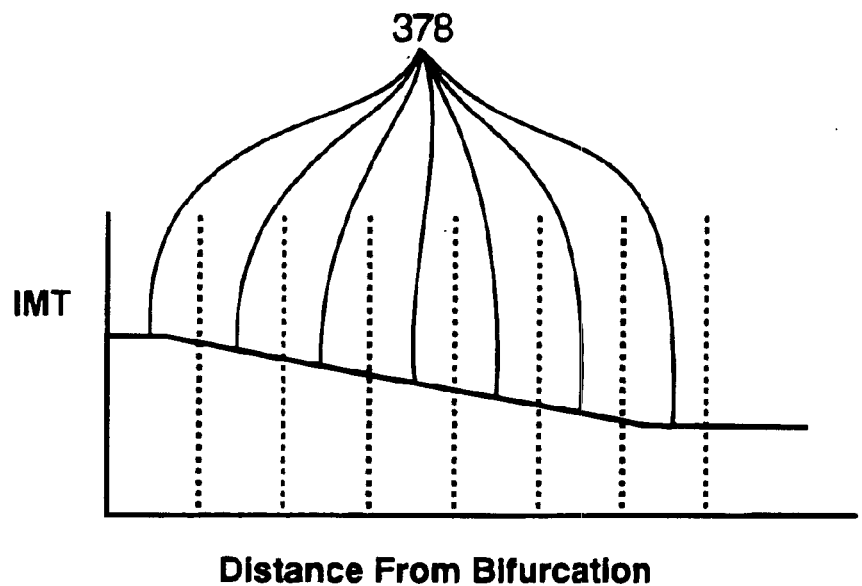
FIG. 27 is a graph representing the IMT measurements taken along a measurement region.

Referring to FIG. 26, while still referring to FIG. 25, the taper compensating module 372 may carry out the taper compensating process 374. The taper compensating process 374 may comprise generating 376 an IMT database 133. Referring to FIG. 27, generating 390 an IMT database 133 may include measuring the IMT of the carotid artery at various subsections 378, and recording the average IMT of each subsection along with its location. In some embodiments, the IMT of the various subsections 378 may be curve fit and a polynomial, or other mathematical description, of the curve fit recorded. The subsections 378 will typically span both segments 94, 98, or portions of both segments 94, 98, in order to include tapering effects near the dilation point 90. The width of the subsections 378 may correlate to the degree of taper, with areas having a large degree of taper being divided into narrower subsections 378. The IMT database 133 typically includes measurements from a large number of patients.

Studies have shown that the degree of taper depends largely on the average IMT, with an artery having a smaller average IMT having less taper than an artery having a larger average IMT. Accordingly, generating 376 the IMT database may include indexing each series of measurements taken from an ultrasound image based on the IMT at a point a standardized distance from the dilation point 90. For example, inasmuch as a segment 98, extending from 10 mm to 20 mm from the dilation point 90, has a substantially constant IMT, measurements taken from an image may be indexed by the IMT at a point 15 mm away from the dilation point 90. Alternatively, the average IMT of a region centered on, or proximate, the 15 mm point may be used.

Furthermore, the IMT measurements of multiple patients having a similar IMT at a standardized point may be averaged together and the average stored for later use, indexed by their average IMT at the standardized point. Typically, the IMT measurement for one patient of a subsection 378 located a specific distance from the dilation point 90 is averaged with the IMT of a subsection 378 at the same distance in an ultrasound image of another patient.

Figure 28:
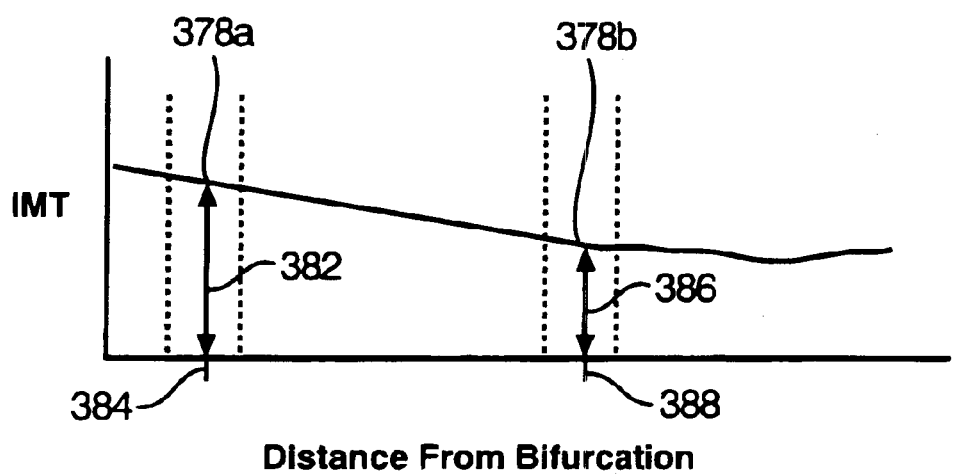
FIG. 28 is a graph illustrating the portions of an IMT measurement used to calculate a normalization factor, in accordance with the invention.

Referring to FIG. 28, while still referring to FIGS. 26 and 27, calculating 380 a normalization factor may include retrieving from the IMT database 133 the IMT measurements 136 taken from a carotid artery, or carotid arteries, having substantially the same IMT thickness as the current ultrasound image at the same point. Thus, for example, if the current ultrasound image has an IMT of 0.27 mm at a point 15 mm from the dilation point 90, calculating 380 a normalization factor may include retrieving IMT measurements 136 for arteries having an IMT of 0.27 mm at the corresponding point. Alternatively, IMT measurements 136 may be retrieved for recorded measurements of arteries having IMT values at the standardized point that bound the IMT of the current artery at that point.

Normalization factors may be calculated 380 based on subsections 378 of stored IMT measurement 136, or measurements 136. For example, a subsection 378a may have an IMT 382 and be located at a point 384. Subsection 378b may have an IMT 386 and be located at another point 388. The point 388 may be chosen to be a standardized distance from the dilation point 90 used to normalize substantially all IMT measurements 136. A normalization factor may be calculated for a subsection 378a by dividing the IMT 386 by the IMT 382. In a like manner, the IMT 386 may be divided by the IMT for each subsection 378 to calculate 380 a normalization factor for each subsection 378.

Figure 29:
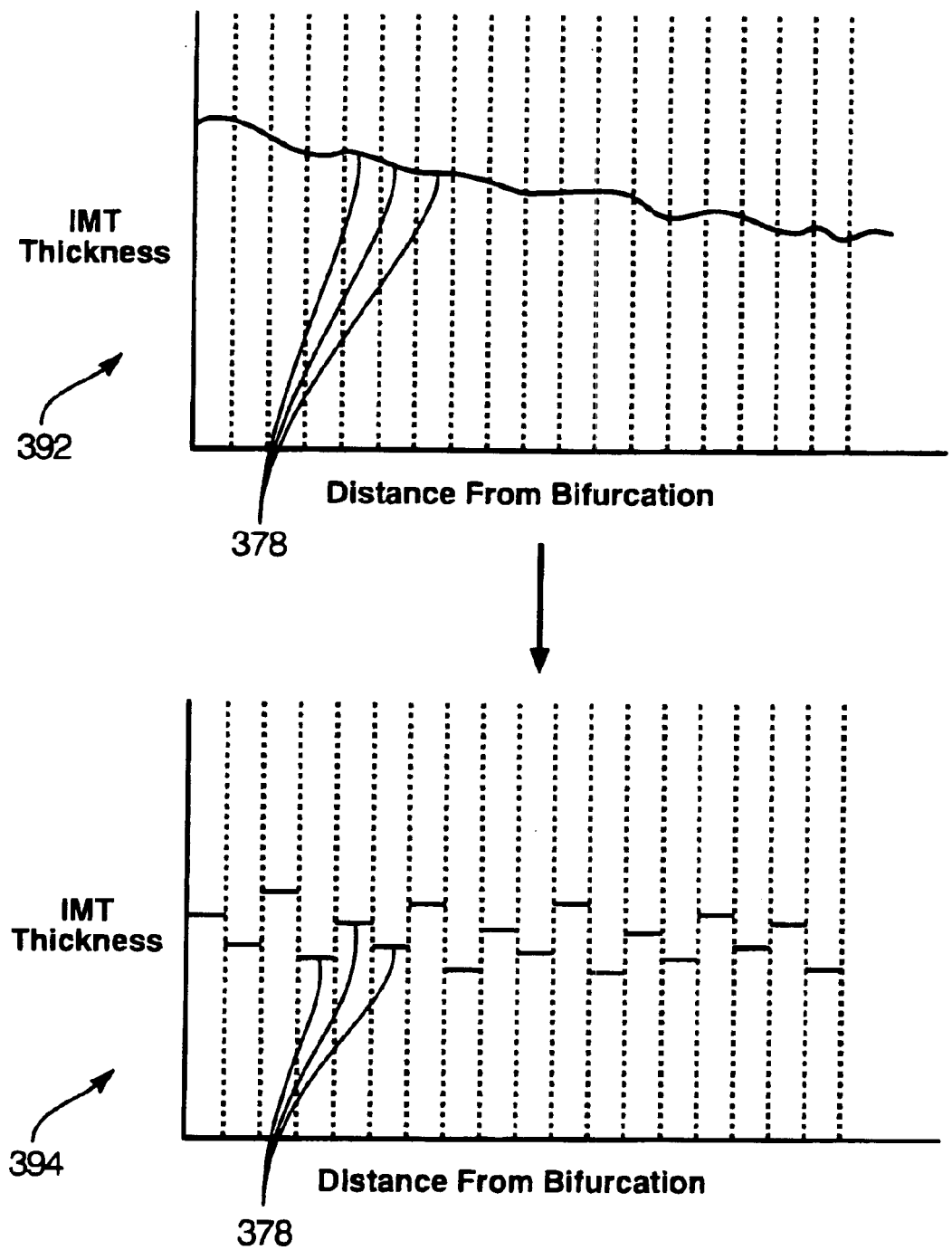
FIG. 29 is a graph illustrating the normalization of IMT thicknesses along a portion of the carotid artery, in accordance with the invention.

Referring again to FIG. 26, applying 390 a normalization factor may include multiplying the normalization factors by the IMT of their corresponding subsections 378 in a current ultrasound image. Thus, for example, a subsection 378 centered at a distance 7 mm from the dilation point 90 in a current image will be multiplied by a normalization factor calculated at a distance 7 mm from the dilation point 90. In this manner, as shown in FIG. 29, the IMT at each subsection 378 in the graph 392 is converted to an approximately equivalent IMT at a standardized point 388 in graph 394. The normalized IMT of each subsection 378 may then be averaged to yield a final value that may be reported.

Various alternative approaches to applying normalization factors are possible. For example, rather than dividing a current ultrasound image into subsections 378, the normalization factors may be applied to the IMT of each column of pixels. An interpolation between normalization factors calculated for subsections 378 centered at locations bounding the horizontal location of a column of pixels may be used to normalized the IMT of a single column of pixels. Alternatively, normalization factors may be calculated for each column of pixels in a retrieved IMT measurement 136. In still other embodiments, a mathematical description of a stored IMT measurement 136 is used to calculate a normalization factor at the location of each column of pixels.

Referring again to FIG. 25, the calculating module 120 may also include a data reduction module 398 and a diagnostic module 400. The data reduction module 398 may compile and statistically analyze IMT measurements and other data to arrive at diagnostic data 131. The diagnostic module 400 may retrieve the diagnostic data 131 in order to relate a patient's IMT with the patient's risk of cardiovascular disease.

What is claimed is:

1. A method for characterizing a blood vessel, having adventitia, media, and intima regions surrounding a lumen, by measuring the apparent intima-media thickness, the method comprising:

provide an image of a blood vessel, the image having a longitudinal direction substantially corresponding to an axial direction of a blood vessel, a lateral direction substantially orthogonal thereto, and comprising pixels each having an intensity associated therewith;

selecting a series of longitudinal positions and finding for each longitudinal position thereof the brightest pixel, having the greatest value of intensity with respect to other pixels positioned laterally therefrom;

defining an adventitia datum by fitting a first curve to the lateral positions of the brightest pixels over a domain of the longitudinal positions;

defining a lumen datum by fitting a second curve to lateral locations of the lumen substantially closest toward the adventitia and corresponding to the longitudinal positions;

defining a media datum by fitting a third curve to pixels, a plurality of which correspond to the location of local minima distributed in a longitudinal direction and positioned between the lumen datum and the adventitia datum;

locating the lumen-intima boundary, extending along the longitudinal direction, as the lateral location of local steepest ascent of intensity in a traverse from the lumen datum toward the media datum;

locating the media-adventitia boundary, extending along the longitudinal direction, as the lateral location of local steepest ascent in intensity in a traverse from the media datum toward the adventitia datum; and calculating the intima-media thickness as the lateral distance between the lumen-intima boundary and the media-adventitia boundary.

2. The method of claim 1, further comprising calibrating the image to provide a measure of distance longitudinally and laterally.

3. The method of claim 1, wherein defining the media datum further comprises fitting a third curve to additional pixels chosen due to location thereof at a distance limit from at least one of the adventitia datum and lumen datum.

4. The method of claim 3, wherein the distance limit is half the distance from the adventitia datum to the lumen datum.

5. The method of claim 1, wherein at least one of the first, second, and third curves is a piecewise fit curve.

6. The method of claim 5, wherein at least one of the first, second, and third curves is fit by a piecewise function selected from a polynomial, a trigonometric function, and an exponential function.

7. The method of claim 6, wherein the piecewise function is a polynomial of an order greater than one.

8. The method of claim 7, wherein the order is greater than two.

9. The method of claim 1, wherein the second curve is a translation of the first curve to a location laterally spaced from the adventitia and at which each pixel thereof has an intensity substantially corresponding to the intensity of the lumen in the image.

10. The method of claim 9, wherein the intensity of pixels corresponding to the lumen datum is a value selected to be above the value of the lowest level of intensity in the image, and above the value of intensity of substantially all pixels corresponding to the lumen proximate the lumen datum and located on a side thereof opposite the adventitia datum.

11. The method of claim 1, wherein the lumen datum corresponds to pixels, each bounded laterally opposite the adventitia by at least three adjacent pixels each having a value of intensity not greater than that of the pixel corresponding thereto in the lumen datum.

12. The method of claim 11, further comprising defining a lumen threshold value corresponding to the lowest value of intensity in the image plus a fraction of the difference of intensity between the highest value of intensity and the lowest value of intensity in the image.

13. The method of claim 1, wherein each pixel corresponding to the lumen datum has an intensity not greater than a lumen threshold value between the intensity of pixels corresponding to the minimum value of intensity in the image and the intensity of pixels corresponding to the maximum value of intensity in the image.

14. The method of claim 13, wherein the lumen threshold value corresponds to a preselected fraction of intensity difference, between that of the adventitia datum and the lumen datum, above the intensity corresponding to the lumen datum.

15. The method of claim 14, wherein the fraction is from about 5 percent to about 25 percent.

16. The method of claim 15, wherein the second curve is the first curve, translated laterally to a position substantially within the portion of the image corresponding to the lumen.

17. The method of claim 1, wherein the second curve has the same shape as the first curve, simply translated laterally to a location at which the intensity of each pixel corresponding thereto is substantially less than a value selected to correspond to an intensity of pixels in the portion of the image corresponding to the lumen.

18. The method of claim 1, wherein the second curve is fit to the lateral positions of pixels having a threshold value of intensity in the image and are bounded by adjacent pixels, on a side thereof opposite the adventitia datum, having substantially no greater value of intensity.

19. The method of claim 1, wherein the third curve comprises a fit of lateral positions of pixels each having a value of intensity representing a local minimum with respect to the lateral direction.

20. The method of claim 19, wherein the local minimum is bounded by a lumen threshold and an adventitia threshold.

21. The method of claim 19, wherein the lateral location of the local minimum is selected to correspond to a pixel found within half the distance from the adventitia datum to the lumen datum.

22. The method of claim 1, further comprising locating a lumen threshold representing a value of intensity proximate the intensity of the minimum value of intensity in a sampling region and an adventitia threshold proximate a value of intensity proximate the minimum value of intensity of pixels in a sampling region.

23. The method of claim 22, wherein the lumen threshold and adventitia threshold differ from the intensity of the minimum value of intensity and the maximum value of intensity, respectively, by a value corresponding to a fraction of the difference between the maximum value of intensity and the minimum value of intensity.

24. The method of claim 23, wherein the preselected value is from about 5 percent to about 25 percent.

25. The method of claim 24, wherein the preselected value is about 10 percent.

26. The method of claim 23, wherein the locations of steepest ascent of intensity are limited to a region of the image containing pixels having intensities between the lumen threshold and the adventitia threshold.

27. The method of claim 26, wherein the third curve is a curve fitted to lateral locations of pixels corresponding to local minimum values of intensity along the longitudinal direction.

28. The method of claim 27, wherein the media datum is adjusted to include only locations of pixels on the third curve or closer to the lumen datum, and each location of a pixel contributing to the third curve and lying between the third curve and the adventitia datum is replaced with the corresponding lateral location on the third curve.

29. A method for finding an intima-media thickness associated with a blood vessel, the method comprising:
providing an image having a longitudinal direction substantially corresponding to an axial direction of a blood vessel and a lateral direction across the axial direction;
the image further comprising locations distributed longitudinally and laterally, each location having an intensity associated therewith and positioned at a unique combination of lateral and longitudinal locations;
selecting a series of longitudinal positions along the longitudinal direction and determining for each such longitudinal position a lateral position at which the image has the greatest intensity;
defining an adventitia datum by fitting a first curve to a range of the lateral positions and a domain of the longitudinal positions;
determining the lateral location of the lumen by identifying for at least one of the longitudinal positions a position corresponding to the lumen;
locating the lumen-intima boundary, extending along the longitudinal direction, as the lateral location of local steepest ascent in intensity, proximate the lateral location of the lumen, in a traverse from the lateral location of the lumen toward the adventitia datum;
locating the media-adventitia boundary, at a plurality of the series of longitudinal positions, as the lateral location of local steepest ascent in intensity, proximate the adventitia datum, in a traverse from the lateral location of the lumen toward the adventitia datum;
calculating the intima-media thickness as the lateral distance between the lumen-intima boundary and the media-adventitia boundary.

30. The method of claim 29, wherein the lateral location of the lumen is determined by identifying the lateral location of at least one pixel having a value of intensity proximate the lowest value of intensity in the image, and being near the adventitia.

31. The method of claim 29, wherein the first curve is a piecewise fit curve.

32. The method of claim 31, wherein the piecewise element used to fit the first curve is selected from a polynomial, a trigonometric function, and an exponential function.

33. The method of claim 32, wherein the piecewise element is a polynomial of greater than first degree.

34. The method of claim 29, further comprising finding a locally high rate of change of intensity as a function of lateral position between the adventitia threshold and the lumen threshold.

35. The method of claim 29, further comprising defining a lumen threshold and adventitia threshold to limit a search for at least one of a local minimum, local maximum, and rate of change of intensity.

36. The method of claim 35, further comprising defining the adventitia threshold as corresponding to a first fraction of a difference between the maximum intensity and the minimum intensity of pixels lying in a portion of the image containing the media/adventitia and lumen/intima boundary.

37. The method of claim 35, further comprising defining a lumen threshold corresponding to a second fraction of a distance laterally between the adventitia datum and the lumen datum.

38. The method of claim 29, wherein the second curve is the first curve, translated laterally.

39. The method of claim 38, wherein determining the lateral location of the lumen comprises defining a measurement region having a rectangular shape and surrounding a portion of a wall of an artery and identifying an edge of the measurement region lying in the lumen as the lateral location of the lumen.

40. A method for finding an intima-media thickness associated with a blood vessel, the method comprising:
providing an image having a longitudinal direction substantially corresponding to an axial direction of a blood vessel and a lateral direction across the axial direction, and comprising locations, distributed longitudinally and laterally, uniquely positioned, and each having an intensity associated therewith;
selecting a series of longitudinal positions along the longitudinal direction and determining for each such longitudinal position a lateral position at which the image has the greatest intensity;
defining an adventitia datum by fitting a first curve to a range of the lateral positions and a domain of the longitudinal positions;
determining the lateral location of the lumen with respect to the adventitia datum;
defining a lumen-intima boundary, and a media-adventitia boundary between the adventitia datum and the lumen;
calculating the intima-media thickness as the lateral distance between the lumen-intima boundary and the media-adventitia boundary.

41. A method for measuring the apparent intima-media thickness of an artery, the method comprising:
Providing an image of an artery wall having lumen, intima, media, and adventitia layers, the image comprising an array of pixels each having an intensity associated therewith and defining rows and columns of pixels with each column defining a longitudinal position and extending across lumen, intima, media, and adventitia layers and with each row defining a lateral position;
identifying an adventitia datum corresponding a curve fit to the lateral position of high intensity pixels in a plurality of columns;
identifying a bounding location, with portions of the lumen, intima, media bounded laterally between the bounding location and the adventitia datum;
identifying a first relatively large intensity gradient proximate the adventitia datum, in a plurality of columns, between the adventitia datum and the bounding location;
identifying a second relatively large intensity gradient proximate the bounding location, in a plurality of columns, between the adventitia datum and the bounding location;
calculating for each of a plurality of columns the lateral distance between the two intensity gradients; and
deriving from the lateral distances a value reflecting an intima-media thickness measurement.

* * * * *